United States Patent
Chou et al.

(10) Patent No.: US 11,806,717 B2
(45) Date of Patent: Nov. 7, 2023

(54) ASSAY USING SAMPLE THICKNESS MULTIPLEXING

(71) Applicant: Essenlix Corporation, Monmouth Junction, NJ (US)

(72) Inventors: Stephen Y. Chou, Princeton, NJ (US); Wei Ding, Princeton, NJ (US); Ji Qi, Hillsborough, NJ (US); Yufan Zhang, Monmouth Junction, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

(21) Appl. No.: 17/268,685

(22) PCT Filed: Aug. 16, 2019

(86) PCT No.: PCT/US2019/046969
§ 371 (c)(1),
(2) Date: Feb. 16, 2021

(87) PCT Pub. No.: WO2020/037304
PCT Pub. Date: Feb. 20, 2020

(65) Prior Publication Data
US 2021/0162402 A1 Jun. 3, 2021

Related U.S. Application Data

(60) Provisional application No. 62/719,018, filed on Aug. 16, 2018.

(51) Int. Cl.
*B01L 3/00* (2006.01)
*G01N 1/28* (2006.01)
*G01N 33/49* (2006.01)

(52) U.S. Cl.
CPC .......... *B01L 3/5088* (2013.01); *G01N 1/2813* (2013.01); *G01N 33/492* (2013.01);
(Continued)

(58) Field of Classification Search
CPC ............ B01L 3/5088; B01L 2200/022; B01L 2200/025; B01L 2300/0636;
(Continued)

(56) References Cited

U.S. PATENT DOCUMENTS

| 6,143,496 A * | 11/2000 | Brown .................. B01L 3/5027 422/504 |
| 7,951,599 B2 | 5/2011 | Levine et al. |
| 2008/0286882 A1 | 11/2008 | Sieben et al. |
| 2009/0238437 A1 * | 9/2009 | Levine .................. G01N 33/49 382/134 |

(Continued)

FOREIGN PATENT DOCUMENTS

| WO | 1999044593 A1 | 9/1999 |
| WO | WO-2017027643 A1 * | 2/2017 ............ B01L 3/5055 |

(Continued)

OTHER PUBLICATIONS

Written Opinion of the International Searching Authority for PCT/US2019/046969 established by the ISA/US completed on Nov. 5, 2019.

(Continued)

*Primary Examiner* — Matthew D Krcha
*Assistant Examiner* — Jacqueline Brazin

(57) ABSTRACT

One aspect of the present invention is to provide the device and methods for performing an assay that uses the multiplexing of sample thicknesses on the same plate. The sample thickness multiplexing can offer many information that are unavailable in using a single sample thickness.

103 Claims, 10 Drawing Sheets

(52) U.S. Cl.
CPC ... *B01L 2200/022* (2013.01); *B01L 2200/025* (2013.01); *B01L 2300/0636* (2013.01); *B01L 2300/0816* (2013.01); *B01L 2300/0829* (2013.01); *B01L 2300/0851* (2013.01); *B01L 2300/0887* (2013.01); *B01L 2300/123* (2013.01); *B01L 2400/0481* (2013.01)

(58) Field of Classification Search
CPC ..... B01L 2300/0816; B01L 2300/0829; B01L 2300/0851; B01L 2300/0887; B01L 2300/123; B01L 2400/0481; B01L 2300/0848; G01N 1/2813; G01N 33/492; G01N 2015/0073; G01N 2015/1006; G01N 2015/1486; G01N 21/6456; G01N 2021/6482
USPC ...................................................... 435/287.1
See application file for complete search history.

(56) References Cited

U.S. PATENT DOCUMENTS

| | | |
|---|---|---|
| 2015/0323519 A1 | 11/2015 | Wardlaw |
| 2016/0136198 A1 | 5/2016 | Lue |
| 2018/0202903 A1* | 7/2018 | Chou .................... B01L 3/5055 |

FOREIGN PATENT DOCUMENTS

| | | |
|---|---|---|
| WO | 2018107105 A1 | 6/2018 |
| WO | 2018148607 A1 | 8/2018 |

OTHER PUBLICATIONS

Zhu et al. "Cost-effective and Rapid Blood Analysis on a Cellphone," Lab On A Chip, Apr. 7, 2013 (Apr. 7, 2013), vol. 13, No. 7, pp. 1282-1288.

* cited by examiner

A

B

ASSAY USING SAMPLE THICKNESS MULTIPLEXING

CROSS-REFERENCE TO RELATED APPLICATIONS

This application is a National Stage entry (§ 371) application of International Application No. PCT/US2019/046969, filed on Aug. 16, 2019, which claims the benefit of priority of U.S. Provisional patent Application No. 62/719,018, filed on Aug. 16, 2018, the contents of which is relied upon and incorporated herein by reference in its entirety. The entire disclosure of any publication or patent document mentioned herein is entirely incorporated by reference.

FIELD

Among other things, the present invention is related to devices and methods of performing biological and chemical assays.

BACKGROUND

In biological and chemical assays, it has a need for new ways to manipulate a sample for improving measurements. The present invention, among other things, provides the devices and methods in manipulating a sample for the purpose of assaying.

SUMMARY

The following brief summary is not intended to include all features and aspects of the present invention.

One aspect of the present invention is to provide the device and methods for performing an assay that uses the multiple sample thicknesses on the same plate.

Another aspect of the present invention is to provide the device and methods that make a sample into a thin layer with different thicknesses at different areas of the layer by sandwiching a sample between two parallel plates and configuring the spacing between the two plates with different spacing height at the different areas of the two plates.

Another aspect of the present invention is to provide the device and methods for performing an assay that uses the multiple sample thicknesses on the same plate, wherein one type(s) of analyte in the sample is measured in one sample thickness while another type(s) of analyte is measured in a different sample thickness. For example, for measuring the cells and other parameters in a whole blood without dilution, the red blood cells and platelets are measured at a sample thickness of about 5 micron (um) where the cells forms a monolayer (using imaging), while the white blood cells and hemoglobin are measured at a sample thickness of about 40 micron.

Another aspect of the present invention is to provide the device and methods for performing an assay that uses the multiple sample thicknesses on the same plate too improve performance of the assays. The improvements includes, but not limited to, the improvement of measurement accuracy, measurement minimum, maximum, dynamic range, linearity range, efficiency, easiness to use, reduction of Hook effects, other assay related parameters, or any combination of thereof.

Another aspect of the present invention is to provide the device and methods for achieving a different spacing height at different areas of the plates by using the spacers with different height at different areas of the plates (hence the sample thickness).

Another aspect of the present invention is to the devices and methods that controls the spacing height (hence the sample thickness at different location) precisely in sub-micron precision and uniformly over a large area.

Another aspect of the present invention is to provide the device and methods to perform an assay with different sample thickness and different assays at different locations of a plate without using a physical fluidic barrier between two different locations. It is achieved by making the vertical spacing height (hence, the sample thickness) is much less than the lateral separation of two locations (e.g. 10 um vertical vs 1 mm lateral), so that the diffusion time between the two location is 10,000 time longer than that vertically.

The term of "CBC" is complete blood count, a complete blood count test measures several components and features of blood including red blood cells, white blood cells, Hemoglobin, Hematocrit, Platelets and others.

Definitions

The terms of "different spacer height" and "different spacing height" are, in the case of QMAX card with spacers in the sample contact areas, interchangeable.

The terms of "analyte" and "targeted analyte" are interchangeable.

The term of "RBC" is red blood cells. The term "WBC" is white blood cells. The term of "HgB" is hemoglobin. The term of "PLT" is platelets. The term of "MCV" is mean corpuscular volume, the average size of red blood cells. The term of "HCT" is hematocrit, the proportion, by volume, of the blood that consists of red blood cells. The term of "WBC differentiate" is white blood cell differentiate, which determines the percentage of each type of white blood cell, including neutrophils, lymphocytes, monocytes, eosinophils and basophils.

BRIEF DESCRIPTION OF THE FIGURES

The skilled artisan will understand that the drawings, described below, are for illustration purposes only. The drawings are not intended to limit the scope of the present teachings in any way. The drawings may not be in scale. In the figures that present experimental data points, the lines that connect the data points are for guiding a viewing of the data only and have no other meaning.

DETAILED DESCRIPTION OF EXEMPLARY EMBODIMENTS

The following detailed description illustrates some embodiments of the invention by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Figure 1:
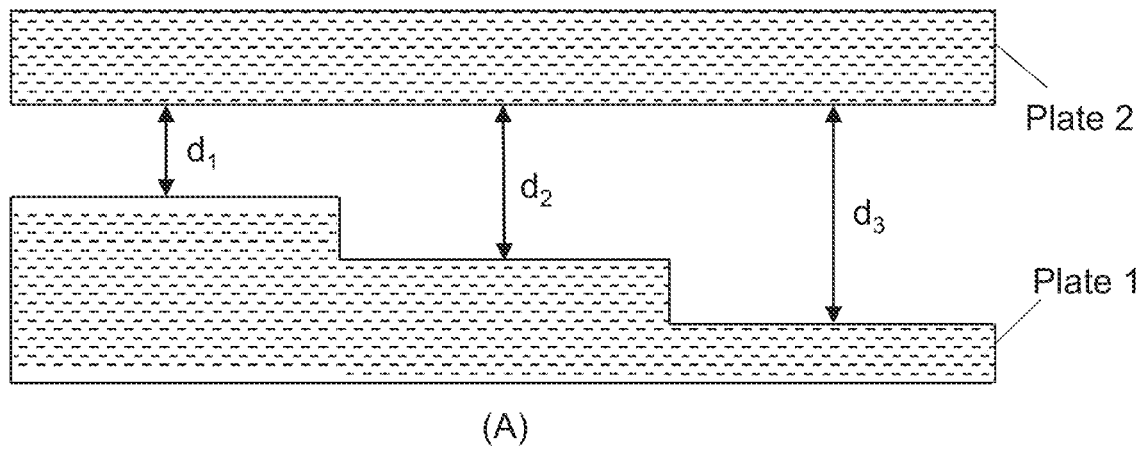
FIG. 1 shows schematics of devices for form a sample layer with different sample thickness at different locations of the sample. In some embodiments, reagent is coated on the plate surface.
Figure 1:
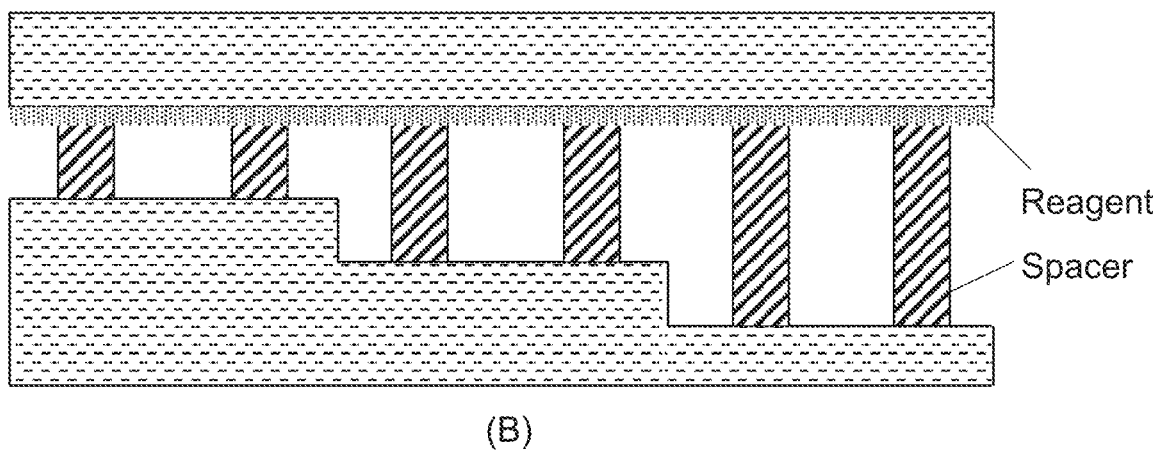
Figure 1:
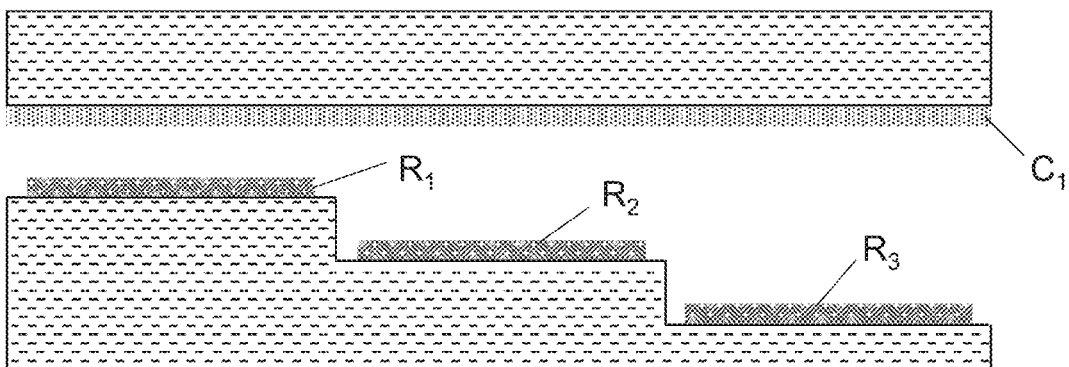

According the present invention, as illustrated in FIG. 1, in some embodiments, a device for analyzing an analyte in a sample, comprising:

a first plate, a second plate, spacers, and at least one imager, wherein:
i. the first and second plates face each other;
ii. the first plate has, on its inner surface, a first and a second sample contact areas at different locations, and the second plate has, on its inner surface, a first and a second sample contact area at different locations that correspond to and face the first and the second sample contact areas of the first plate, respectively, wherein the sample contact areas are the areas for contacting a sample that contains or is suspected to contain an analyte;
iii. the spacers are between the first plate and the second plate;
iv. the spacers and the surface of the sample contact areas are configured to (a) make a first spacing height and a second spacing height different from each other, wherein the first spacing height is the spacing between the first sample contact surface on the first plate and its corresponding sample contact area on the second plate, and the second spacing height is the spacing between the second sample contact surface on the first plate and its corresponding sample contact are on the second plate, wherein the first and second spacing heights are 250 um or less; and
v. the at least one imager is configured to image the samples in the first and second sample contact area, and to measure an optical signal related to the analyte in the first and second spacing.

FIG. 1 illustrates several exemplary embodiments of the present invention. In panel (A), it shows schematics of devices form a sample layer with three different sample thickness d1, d2 and d3 at three different locations of the sample. In panel (B), it shows that spacers with three heights form a sample layer with three different sample thickness at three different locations of the sample and the reagent is coated on one of the plate, and in Panel (C), three different reagents R1, R2, R3 are coated at plate 1 at three locations of three different sample thickness, while one same reagent C1 is coated at plate 2 over three locations.

A.1 CBC Using QMAX-Card with Different Spacing Height

In performing CBC (complete blood count) by imaging method, it is advantageous to control the height of a thin blood layer thickness. In the present invention, in some embodiments, a QMAX device with two or more spacer heights do CBC by imaging, wherein one QMAX card is configured to measure more than one type of blood cells, and wherein some type of the blood cells and/or blood parameters (e.g. white cells and hemoglobin) measured in one spacer height area and other blood cells and/or parameters are measured in another spacer height area of the same plate (different spacer height areas give different sample thickness). [spacing height area]

According to the present invention, in some embodiments, a device for analyzing an
analyte in a whole blood sample, comprising:
a first plate, a second plate, spacers, and at least one imager, wherein:
i. the first and second plates face each other;
ii. the first plate has, on its inner surface, a first and a second sample contact areas at different locations, and the second plate has, on its inner surface, a first and a second sample contact area at different locations that correspond to and face the first and the second sample contact areas of the first plate, respectively, wherein the sample contact areas are the areas for contacting a sample that contains or is suspected to contain an analyte;
iii. the spacers are between the first plate and the second plate;
iv. the spacers and the surface of the sample contact areas are configured to (a) make a first spacing height and a second spacing height different from each other, wherein the first spacing height is the spacing between the first sample contact surface on the first plate and its corresponding sample contact area on the second plate, and the second spacing height is the spacing between the second sample contact surface on the first plate and its corresponding sample contact are on the second plate, wherein the first and second spacing heights are 250 um or less; and v. the at least one imager is configured to image the samples in the first and second sample contact area, and to measure an optical signal related to the analyte in the first and second spacing;

wherein the sample is whole blood, and the analyte comprises red blood cells, white blood cells, and platelets, wherein the first spacing height is a single value selected from a range of 3.5 um to 6.5 um, and the second spacing height is a single value selected from a range of 10 um to 120 um, and wherein the first spacing height is used to measure the red blood cell and the platelets, and the second spacing height is used to measure the white blood cells and hemoglobin of the red blood cell.

In some embodiments, a device for performing different blood cell types and/or different blood cell parameters, comprises a QMAX device of any embodiment that has at least two areas that each has a different spacer height, whereas one blood cell type and/or parameter is imaged in one of the spacer height area, and another blood cell type and/or parameter is imaged in another spacer height area.

In some embodiments, a method for performing different blood cell types and/different blood cell parameters, comprising:

(a) obtaining a blood sample;
(b) obtaining a device of any embodiment of a QMAX device comprising two or more different spacer height areas;
(c) depositing the sample on one or both of the plates when the plates are in the open configuration,
(d) after (c), bringing the two plates together and pressing the plates into a closed configuration,
(e) after (d), measuring the sample using imaging, wherein the blood sample is measured in at least two different spacer height area.

In some embodiments, the blood is whole blood. In some embodiments, the blood is whole blood without significant dilution. In some embodiments, the blood is whole blood with dilution.

A device for analyzing blood cells in a blood sample, comprising:

a first plate, a second plate, spacers, and adaptor wherein:
  i. the plates are movable relative to each other into different configurations;
  ii. one or both plates are flexible;
  iii. each of the plates comprises an inner surface that has a sample contact area for contacting a fluidic sample;
  iv. one or both of the plates comprise the spacers that are permanently fixed on the sample contact area of a respective plate;
  v. the spacers have at least two areas that each has a different spacer height that has a value selected in the range of 1 um to 50 um;
  vi. the spacers in each area have:
    (a) a predetermined substantially uniform height that has a value selected in the range of 1 um to 50 um,
    (b) a shape of pillar with substantially uniform cross-section and a flat top surface;
    (c) a ratio of the width to the height equal or larger than one;
    (d) a predetermined fixed, non-random, inter-spacer distance that is in the range of 10 um to 200 um;
    (e) a filling factor of equal to 3% or larger, wherein the filling factor is the ratio of the spacer contact area (on the plate) to the total plate area; and
    (f) the filling factor multiplies the Young's modulus of the spacer is equal to 2 MPa or larger;
  vii. one or both of the plates comprise the reagents that are coated on the sample contact area of a respective plate;
  viii. the adaptor comprises: (a) a housing, (b) an attachment member on the housing that allows the adaptor to be attached to a mobile phone with a camera, (c) a slot in the housing that allows (1) the plates in a closed configuration to slide into the slot and (2) when the plates are in the slot, at least a part of the sample area is less than 2 cm away from the outer surface of the camera, and (d) an optical system in the housing configured to have at least a part of the sample contact area be imaged by the camera;

wherein one of the configurations is an open configuration, in which: the two plates are partially or completely separated apart, the spacing between the plates is not regulated by the spacers, and the sample is deposited on one or both of the plates; and wherein another of the configurations is a closed configuration which is configured after the sample is deposited in the open configuration; and in the closed configuration: at least part of the sample is compressed by the two plates into a layer of highly uniform thickness and is substantially stagnant relative to the plates, wherein the uniform thickness of the layer is confined by the sample contact areas of the two plates and is regulated by the plates and the spacers.

In some embodiments, one spacer height area is configured to create a blood layer of about 5 um, and another spacer height area is configured to create a blood layer of about 30 um.

In some embodiments, one spacer height area is configured to create a blood layer between 1.5 um and 4 um, and another spacer height area is configured to create a blood layer of between 25 um and 35 um.

In some embodiments, one spacer height area is configured to create a blood layer between 4 um and 6 um, and another spacer height area is configured to create a blood layer of between 25 um and 35 um.

In some embodiments, the spacer height 5 um is for RBC, WBC, PLT, MCV; and the spacer height 30 um is for WBC, HgB; and the spacer height 5 um and 30 um combination is for MCH, MCHC and others.

In some embodiments, the spacer height 1.5 um to 6.0 um is for RBC, WBC, PLT, MCV; and the spacer height 10 um to 20 um is for WBC, HgB; and the spacer height 5 um and 30 um combination is for MCH, MCHC and others.

In some embodiments, the spacer height 1.5 um to 3 um is for RBC, WBC, PLT, MCV; and the spacer height 10 um to 20 um is for WBC, HgB; and the spacer height 5 um and 30 um combination is for MCH, MCHC and others.

In some embodiments, the spacer height 3 um to 6 um is for RBC, WBC, PLT, MCV; and the spacer height 25 um to 35 um is for WBC, HgB; and the spacer height 5 um and 30 um combination is for MCH, MCHC and others.

In some embodiments, the spacer height 3 um to 6 um is for RBC, WBC, PLT, MCV; and the spacer height 10 um to 32 um is for WBC, HgB; and the spacer height 5 um and 30 um combination is for MCH, MCHC and others.

In some embodiments, the spacer height 1.5 um to 8 um is for RBC, WBC, PLT, MCV; and the spacer height 10 um to 50 um is WBC, HgB; and the spacer height 5 um and 30 um combination is for MCH, MCHC and others.

In some embodiments, the spacer height area with lower spacer height is for RBC, WBC, PLT, MCV; and the spacer height area with higher spacer height is WBC, HgB; and the combination is for MCH, MCHC and others.

In some embodiments, the shape of one spacer height area is round, ellipse, rectangle, triangle, polygonal, ring-shaped, or any superposition of these shapes.

In some embodiments, the preferred shape of one spacer height area is round and ellipse.

In some embodiments, the spacer height areas on the plates are configured and/or arranged in an array form, and the array is a periodic, non-periodic array or periodic in some locations of the plate while non-periodic in other locations.

In some embodiments, the periodic array of the spacers is in 1 dimensional or 2 dimensional.

In some embodiments, the periodic array of the spacers is arranged as lattices of square, rectangle, triangle, hexagon, polygon, or any combinations of thereof, where a combination means that different locations of a plate has different spacer lattices.

In some embodiments, the spacer heights areas on the plates are configured and/or arranged in an array form, and the array is a periodic with a periodicity of 0.1 mm, 0.2 mm, 0.5 mm, 0.8 mm, 1.0 mm, 1.5 mm, 2.0 mm, 2.5 mm, 3 mm, 5 mm, 10 mm or in a range between any two of the values.

In some embodiments, the spacer heights areas on the plates are configured and/or arranged in an array form, and the array is a periodic with a preferred periodicity of 0.2 mm, 0.5 mm, 0.7 mm, 0.8 mm, 1.0 mm, 1.5 mm, 2 mm or in a range between any two of the values.

In some embodiments, the spacer height areas on the plates are configured and/or arranged in an array form, and the array is a periodic with a preferred periodicity of half of the field of view of the imaging system.

In some embodiments, the spacer heights areas on the plates are configured and/or arranged in an array form, and the array is a periodic with a preferred periodicity of 0.1, 0.2, 0.3, 0.5, 0.8, 0.9, 1.0 or in a range between any two of the values of the field of view from the imaging system.

In some embodiments, the spacer lateral dimensions 10 um to 20 um is for RBC, WBC, PLT, MCV in one area; and the spacer lateral dimensions 30 um to 40 um is for WBC, HgB in another area.

In some embodiments, the spacer lateral dimensions 30 um to 40 um is for RBC, WBC, PLT, MCV in one area; and the spacer lateral dimensions 30 um to 40 um is for WBC, HgB in another area.

In some embodiments, the spacer lateral dimensions 10 um to 20 um is for RBC, WBC, PLT, MCV in one area; and the spacer lateral dimensions 30 um to 40 um is for WBC, HgB in another area.

In some embodiments, the spacer lateral dimensions 10 um to 50 um is for RBC, WBC, PLT, MCV in one area; and the spacer lateral dimensions 10 um to 50 um is for WBC, HgB in another area.

In some embodiment, there are two spacer heights areas on the plates. In some embodiment, there are two kinds of spacer heights areas on the plates. In some embodiment, there are more than two kinds of spacer heights areas on the plates.

In some embodiment, the edge to edge distance of any two closest spacing height areas is 0 um, 5 um, 10 um, 30 um, 50 um, 100 um, 500 um, 1 mm, 2 mm, 3 mm, 5 mm or in a range between any two of the values. In some embodiment, the preferred edge to edge distance of any two closest spacing height areas is 0 um, 5 um, 10 um, 30 um, 50 um, 100 um, 500 um, 1 mm, or in a range between any two of the values.

In some embodiment, the manufacturing of the plate use imprint lithography. In some embodiment, the manufacturing of the plate use injection molding.

In some embodiments, the device, kit, system, or method of any prior embodiments, wherein the chemicals are coated with same concentration in all spacer height areas.

In some embodiments, the device, kit, system, or method of any prior embodiments, wherein the chemicals are coated with a different concentration in different spacer height areas.

The device, kit, system, or method of any prior embodiments, wherein the dye to stain the WBC is coated onto the first plate, or the second plate or both.

The device, kit, system, or method of any prior embodiments, wherein the dye to stain the WBC and PLT is coated onto the first plate, the second plate, or both.

The device, kit, system, or method of any prior embodiments, wherein the dye to stain the PLT is coated onto the first plate, the second plate, or both.

The device, kit, system, or method of any prior embodiments, wherein the reagent is coated by droplet printing into an array.

The device, kit, system, or method of any prior embodiments, wherein the reagent is coated by spray.

The device, kit, system, or method of any prior embodiments, wherein the reagent is coated by contact printing.

The device, kit, system, or method of any prior embodiments, wherein the reagent is coated by transfer printing.

The device, kit, system, or method of any prior embodiments, wherein the acridine orange is coated at one spacer height area on the plate with an area concentration of 3 to 10 ng/mm$^2$ and Zwittergent is coated at one spacer height area on the plate with an area concentration of 3 to 30 ng/mm$^2$.

The device, kit, system, or method of any prior embodiments, wherein the acridine orange is coated on the plate at one spacer height area with an area concentration of 10 to 80 ng/mm$^2$ and Zwittergent is coated on the plate at one spacer height area with an area concentration of 20 to 130 ng/mm$^2$.

The device, kit, system, or method of any prior embodiments, wherein the reagent is dissolved in organic solvent as alcohol, ethylether, hexane, tetrachloroethane, toluene, and xylene.

The device, kit, system, or method of any prior embodiments, wherein the reagent is coated by the different wetting properties of coating reagent at different pillar height area of the plate.

The device, kit, system, or method of any prior embodiments, wherein the dye to stain the RBC is coated onto at least on spacer height area.

The device, kit, system, or method of any prior embodiments, wherein the surfactant to separate and round RBC is coated onto at least on spacer height area.

The device, kit, system, or method of any prior embodiments, wherein the chemical to lyse RBC is coated onto at least on spacer height area.

The device, kit, system, or method of any prior embodiments, wherein the acridine orange is coated onto at least on spacer height area.

The device, kit, system, or method of any prior embodiments, wherein the Zwittergent is coated onto at least on spacer height area.

The device, kit, system, or method of any prior embodiments, wherein the Methylene blue and Zwittergent is coated onto at least on spacer height area.

The device, kit, system, or method of any prior embodiments, wherein the acridine orange and Zwittergent is coated onto at least on spacer height area.

The device, kit, system, or method of any prior embodiments, wherein the YOYO dye and Zwittergent is coated onto at least on spacer height area.

The devices or methods of any prior embodiment, wherein the device further comprises, at least on spacer height area, multi reagent layers including anti-conglutination, cell lysing, cell staining, release time control material layers, and their combinations;

wherein each layer coated on the plates has a thickness of 10 nm, 100 nm, 200 nm, 500 nm, 1 um or a range between any two of the values.

where anti-conglutination agent comprises ethylenediaminetetraacetic acid (EDTA), EDTA disodium, K2EDTA, K3EDTA, and etc.

wherein cell stain agent comprise Wright's stain (Eosin, methylene blue), Giemsa stain (Eosin, methylene blue, and Azure B), May-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (BO21) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride), YOYO.

wherein cell stain agent comprise Wright's stain (Eosin, methylene blue), Giemsa stain (Eosin, methylene blue, and Azure B), May-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (BO21) dye, Ethidium Bromide, Brilliant Sulfaflavine and a Stilbene Disulfonic Acid derivative, Erythrosine B or trypan blue, Hoechst 33342, Trihydrochloride, Trihydrate, and DAPI (4',6-Diamidino-2-Phenylindole, Dihydrochloride), YOYO, acid fuchsine, hematoxylin, Hoechst stains including Hoechst 33258 and Hoechst 33342, methyl green, methylene blue, Nile blue, Nile red, osmium tetraoxide, rhodamine, safranine, MeOSuc-AAPV-AMC, CFSE, BCECF/AM, silver nitrate, neutral red, pyronin Y, Calcein-AM, Dihydroethidium, Xylene Cyanol FF, Rhodamine 123, 4-Methylumbelliferyl palmitate, Fast Blue B Salt, Lucifer Yellow CH dipotassium salt, DAPI dilactate, Propidium Iodide; wherein cell lysing agent comprise ammonium chloride, sodium bicarbonate, ethylenediaminetetraacetic acid (EDTA), acetic acid, citric acid, other acid and base, and etc. wherein release time control material comprise albumin, carbomers, carboxymethyl cellulose, carrageenan, chitosan, dextrin, polyethylene glycol, polyvinylpyrrolidone, polyvinyl alcohol, and like materials. In some embodiment, chemicals with certain concentration is coated on the plate at least on spacer height area and dissolved into the blood to achieve a uniform distribution of red blood cell in device.

In some embodiment, chemicals with certain concentration is coated on the plate at least on spacer height area and dissolved into the blood to lyse the red blood cell in device, wherein the coating can be on first plate, or second plate, or both.

In some embodiment, the chemicals coated at least on spacer height area in the device including but not limit to Surfactant, Zwittergent, ASB-14, ASB-16, CHAPS, Cationic surfactant NN-[Tris(hydroxymethyl) methyl]-N-alkyl-N,N-dimethyl ammonium chloride (IIa), IIb, IIc, IId, CTAC, Tween 20, Tween 40, Tween 60, Tween 80, Sodium lauryl sulfate (SLS), ammonium lauryl sulfate, CTAB, sodium lauryl ether sulfate (SLES), sodium myreth sulfate, docusate, perfluorooctanesulfonate, alkyl-aryl ether phosphates, alkyl ether phosphates, CTAB, cetylpyridinium chloride (CPC), benzalkonium chloride (BAC), benzethonium chloride (BZT), dimethyldioctadecylammonium chloride, dioctadecyldimethlyammonium bromide (DODAB), cocamidopropyl hydroxysultaine, cocamidopropyl betaine, narrow-range ethoxylate, octaethylene glycol monododecyl ether, pentaethylene glycol monododecyl ether, nonxynols, Triton X-100, polyethoxylated tallow amine, cocamide monoethanolamine, cocamide diethanolamine, poloxamers, glycerol monostearate, glycerol monolaurate, sorbitan monolaurate, sorbitan monostearate, sorbitan tristearate, decyl glucoside, lauryl glucoside, octyl glucoside, lauryldimethylamine oxide, dimethyl sulfoxide, phosphine oxide.

In some embodiment, the reagent causing red blood cell lysis coated in the device including but not limit to Pluronic F-127, Cremophor EL, Pluronic F-68, Myrj 52, Brij 35, sodium oleate, sodium dodecyl sulfate, Tween 20, Tween 40, Tween 60, Tween 80, SLS, CTAB, CTAC, Tamoxifen, saponin, hydrochloric acid, sulfuric acid, nitric acid, phosphoric acid, lactic acid, ABS-14, ABS-16, anti-malaria drugs (quinine compounds), arsenic, dapsone, metals (chromium/chromates, platinum salts, nickel compounds, copper, lead, cis-platinum), nitrites, nitrofurantoin, penicillin, phenazopyridine (pyridium), rho immune globulin, ribavirin, sulfonamides, sulfones.

In some embodiment, the anticoagulant coated in the device including but not limit to EDTA such as dipotassium ethylenediaminetetraacetic acid (K2EDTA), tripotassium ethylenediaminetetraacetic (K3EDTA), coumarins (vitamin K antagonists), warfarin (coumadin), acenocoumarol, phenprocoumon, atromentin, phenindione, heparin, fondaparinux and idraparinux, dabigatran, rivaroxaban, apixaban, edoxaban, betrixaban, NOACs, hirudin, lepirudin, bivalirudin, agratroban, dabigatran, batroxobin, hementin, Vitamin E, sodium citrate, acid citrate dextrose, oxalate such as fluoride oxalate, deltaparin, desirudin, enoxaparin.

In some embodiment, to achieve a uniform distribution of red blood cell in device, Zwittergent is coated on the plate at least on spacer height area with a preferred area concentration of 3 ng/mm$^2$, 5 ng/mm$^2$, 8 ng/mm$^2$, 12 ng/mm$^2$, 15 ng/mm$^2$, 25 ng/mm$^2$, 35 ng/mm$^2$, 50 ng/mm$^2$, 80 ng/mm$^2$, 150 ng/mm$^2$ or in a range between any of the two values.

In some embodiment, to lyse red blood cells in the device, Zwittergent is coated on the plate at least on spacer height area with a preferred area concentration of 100 ng/mm$^2$, 120 ng/mm$^2$, 150 ng/mm$^2$, 180 ng/mm$^2$, 200 ng/mm$^2$, 300 ng/mm$^2$, 400 ng/mm$^2$, 500 ng/mm$^2$, 800 ng/mm$^2$, 1000 ng/mm$^2$ or in a range between any of the two values.

In some embodiment, to achieve a uniform distribution of red blood cells in the device, Zwittergent is coated on the plate at least on spacer height area with a preferred final concentration in blood of 0.05 mg/mL, 0.1 mg/mL, 0.2 mg/mL, 0.3 mg/mL, 0.5 mg/mL, 0.6 mg/mL, 1.0 mg/mL, 2 mg/mL or in a range between any of the two values.

In some embodiment, to lyse red blood cells in the device, Zwittergent is coated on the plate at least on a spacer height area with a preferred final concentration in blood of 2 mg/mL, 3 mg/mL, 4 mg/mL, 5 mg/mL, 6 mg/mL, 7 mg/mL, 9 mg/mL, 10 mg/mL, 15 mg/mL, 25 mg/mL, 50 mg/mL, or in a range between any of the two values.

In some embodiment, to achieve a uniform distribution of red blood cells in the device, Zwittergent is coated on the plate at least on a spacer height area with a preferred area concentration of 3 ng/mm$^2$, 5 ng/mm$^2$, 8 ng/mm$^2$, 12 ng/mm$^2$, 15 ng/mm$^2$, 25 ng/mm$^2$, 35 ng/mm$^2$, 50 ng/mm$^2$, 80 ng/mm$^2$, 100 ng/mm$^2$, or in a range between any of the two values.

In some embodiment, to lyse red blood cells in the device, Zwittergent is coated on the plate at least on spacer height area with a preferred area concentration of 100 ng/mm$^2$, 120 ng/mm$^2$, 150 ng/mm$^2$, 180 ng/mm$^2$, 200 ng/mm$^2$, 300 ng/mm$^2$, 400 ng/mm$^2$, 500 ng/mm$^2$, 800 ng/mm$^2$, 1000 ng/mm$^2$, or in a range between any of the two values.

In some embodiment, to achieve a uniform distribution of red blood cells in the device, Zwittergent is coated on the plate at least on spacer height area with a preferred final concentration in blood of 0.05 mg/mL, 0.1 mg/mL, 0.2 mg/mL, 0.3 mg/mL, 0.5 mg/mL, 0.6 mg/mL, 1.0 mg/mL, 2 mg/mL, or in a range between any of the two values.

In some embodiment, to lyse red blood cells in the device, Zwittergent is coated on the plate at least on spacer height area with a preferred final concentration in blood of 2 mg/mL, 3 mg/mL, 4 mg/mL, 5 mg/mL, 6 mg/mL, 7 mg/mL, 9 mg/mL, 10 mg/mL, 15 mg/mL, 25 mg/mL, 50 mg/mL, or in a range between any of the two values.

The device, kit, system, or method of any prior embodiments, wherein the acridine orange is coated on the plate at least on a spacer height area with an area concentration of 0.5 ng/mm$^2$, 1 ng/mm$^2$, 2 ng/mm$^2$, 3 ng/mm$^2$, 5 ng/mm$^2$, 8 ng/mm$^2$, 10 ng/mm$^2$, 15 ng/mm$^2$, 20 ng/mm$^2$, 30 ng/mm$^2$, or in a range between any of the two values.

The device, kit, system, or method of any prior embodiments, wherein the acridine orange is coated on the plate with an area concentration of 3 to 10 ng/mm$^2$, and the Zwittergent is coated on the plate with an area concentration of 3 to 10 ng/mm$^2$.

The device, kit, system, or method of any prior embodiments, wherein the acridine orange is coated on the plate with an area concentration of 5 to 20 ng/mm$^2$, and the Zwittergent is coated on the plate with an area concentration of 10 to 30 ng/mm$^2$.

For an open-spacer, the lateral dimensions can be characterized by its lateral dimension (sometimes called width) in the x and y—two orthogonal directions. The lateral dimension of a spacer in each direction is the same or different. In some embodiments, the lateral dimension for each direction (x or y) is 1 nm or less, 3 nm or less, 5 nm or less, 7 nm or less, 10 nm or less, 20 nm or less, 30 nm or less, 40 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, or 500 µm or less, or in a range between any two of the values.

In some embodiments, the lateral dimension of a spacer is between 5 um and 10 um.

In some embodiments, the lateral dimension of a spacer is between 10 um and 15 um. In some embodiments, the lateral dimension of a spacer is between 15 um and 20 um.

In some embodiments, the lateral dimension of a spacer is between 20 um and 25 um.

In some embodiments, the lateral dimension of a spacer is between 25 um and 30 um.

In some embodiments, the lateral dimension of a spacer is between 30 um and 40 um.

In some embodiments, the lateral dimension of a spacer is between 40 um and 50 um.

In some embodiments, the lateral dimension of a spacer is between 50 um and 70 um.

In some embodiments, the lateral dimension of a spacer is between 70 um and 90 um.

In some embodiments, the lateral dimension of a spacer is between 90 um and 120 um.

In some embodiments, the lateral dimension of a spacer is between 20 times and 40 times of the central wavelength of the incident light.

In some embodiments, the lateral dimension of a spacer is between 40 times and 80 times of the central wavelength of the incident light.

In some embodiments, the lateral dimension of a spacer is between 80 times and 120 times of the central wavelength of the incident light.

In some embodiments, the lateral dimension of a spacer is between 120 times and 80 times of the central wavelength of the incident light.

In some embodiments, the ratio of the lateral dimensions of x to y direction is 1, 1.5, 2, 5, 10, 100, 500, 1000, 10,000, or in a range between any two of the value. In some embodiments, a different ratio is used to regulate the sample flow direction; the larger the ratio, the flow is along one direction (larger size direction).

In some embodiments, different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height of the spacers are substantially the same. In some embodiments, all spacers have the same shape and dimensions. In some embodiments, the spacers have different lateral dimensions.

For enclosed-spacers, in some embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

In certain embodiments, the aspect ratio of the height to the average lateral dimension of the pillar spacer is 100,000, 10,000, 1,000, 100, 10, 1, 0.1, 0.01, 0.001, 0.0001, 0, 00001, or in a range between any two of the values.

In some embodiments, all spacers in one spacer height area have the same pre-determined height. In some embodiments, spacers in one spacer height area have different pre-determined heights. In some embodiments, spacers can be divided into groups or regions, wherein each group or region has its own spacer height. And in certain embodiments, the predetermined height of the spacers in one spacer height area is an average height of the spacers. In some embodiments, the spacers in one spacer height area have approximately the same height. In some embodiments, a percentage of number of the spacers in one spacer height area have the same height.

The height of the spacers in one spacer height area is selected by a desired regulated spacing between the plates and/or a regulated final sample thickness and the residue sample thickness. The spacer height (the predetermined spacer height), the spacing between the plates, and/or sample thickness is 3 nm or less, 10 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, 500 µm or less, 800 µm or less, 1 mm or less, 2 mm or less, 4 mm or less, or in a range between any two of the values.

The spacer height, the spacing between the plates, and/or sample thickness in one spacer height area is between 1 nm to 100 nm in one preferred embodiment, 100 nm to 500 nm in another preferred embodiment, 500 nm to 1000 nm in a separate preferred embodiment, 1 µm (i.e. 1000 nm) to 2 µm in another preferred embodiment, 2 µm to 3 µm in a separate preferred embodiment, 3 µm to 5 µm in another preferred embodiment, 5 µm to 10 µm in a separate preferred embodiment, and 10 µm to 50 µm in another preferred embodiment, 50 µm to 100 µm in a separate preferred embodiment.

The spacer height, the spacing between the plates, and/or sample thickness in one spacer height area is between 1.5 um to 2.5 um in one preferred embodiment.

The spacer height, the spacing between the plates, and/or sample thickness in one spacer height area is between 2.5 um to 4 um in one preferred embodiment.

The spacer height, the spacing between the plates, and/or sample thickness in one spacer height area is between 4 um to 6 um in one preferred embodiment.

The spacer height, the spacing between the plates, and/or sample thickness in one spacer height area is between 6 um to 10 um in one preferred embodiment.

The spacer height, the spacing between the plates, and/or sample thickness in one spacer height area is between 10 um to 15 um in one preferred embodiment.

The spacer height, the spacing between the plates, and/or sample thickness in one spacer height area is between 15 um to 25 um in one preferred embodiment.

The spacer height, the spacing between the plates, and/or sample thickness in one spacer height area is between 25 um to 35 um in one preferred embodiment.

The spacer height, the spacing between the plates, and/or sample thickness in one spacer height area is between 35 um to 50 um in one preferred embodiment.

The spacer height, the spacing between the plates, and/or sample thickness in one spacer height area is between 50 um to 100 um in one preferred embodiment.

The spacer height, the spacing between the plates, and/or sample thickness in one spacer height area is between 100 um to 150 um in one preferred embodiment.

The spacer height, the spacing between the plates, and/or sample thickness in one spacer height area is between 150 um to 200 um in one preferred embodiment.

The spacer height in one spacer height area is related to and limited by the incident light source power density when testing the whole blood sample.

In one preferred embodiment, with incident light source power of 0.1 W/cm$^2$ to 5 W/cm$^2$, the spacer height, the spacing between the plates, and/or sample thickness in one spacer height area is less than 2 um, less than 5 um, less than 10 um.

In one preferred embodiment, with incident light source power of 0.1 W/cm$^2$ to 5 W/cm$^2$, the spacer height, the spacing between the plates, and/or sample thickness in one spacer height area is less than 10 um, less than 20 um, less than 30 um.

In one preferred embodiment, with incident light source power of 0.1 W/cm$^2$ to 5 W/cm$^2$, the spacer height, the spacing between the plates, and/or sample thickness in one spacer height area is less than 30 um, less than 40 um, less than 50 um.

In one preferred embodiment, with incident light source power of 5 W/cm$^2$ to 50 W/cm$^2$, the spacer height, the spacing between the plates, and/or sample thickness in one spacer height area is less than 10 um, less than 20 um, less than 30 um.

In one preferred embodiment, with incident light source power of 5 W/cm$^2$ to 50 W/cm$^2$, the spacer height, the spacing between the plates, and/or sample thickness in one spacer height area is less than 30 um, less than 40 um, less than 50 um.

In one preferred embodiment, with incident light source power of 5 W/cm$^2$ to 50 W/cm$^2$, the spacer height, the spacing between the plates, and/or sample thickness in one spacer height area is less than 50 um, less than 100 um, less than 150 um, less than 200 um.

In one preferred embodiment, with incident light source power of 50 W/cm$^2$ to 500 W/cm$^2$, the spacer height, the spacing between the plates, and/or sample thickness in one spacer height area is less than 50 um, less than 100 um, less than 150 um, less than 200 um.

In some embodiments, the spacer height in one spacer height area is controlled precisely. The relative precision of the spacer (i.e. the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or in a range between any of the values.

In some embodiments, the spacer height, the spacing between the plates, and/or sample thickness in one spacer height area is: (i) equal to or slightly larger than the minimum dimension of an analyte, or (ii) equal to or slightly larger than the maximum dimension of an analyte. The "slightly larger" means that it is about 1% to 5% larger and any number between the two values.

In some embodiments, the spacer height, the spacing between the plates, and/or sample thickness in one spacer height area is larger than the minimum dimension of an analyte (e.g. an analyte has an anisotropic shape), but less than the maximum dimension of the analyte.

For example, the red blood cell has a disk shape with a minim dimension of 2 µm (disk thickness) and a maximum dimension of 11 µm (a disk diameter). In an embodiment of the present invention, the spacers in one spacer height area can be selected to make the inner surface spacing of the plates in a relevant area, for example, 2 µm (equal to the minimum dimension), 2.2 µm, or 3 (50% larger than the minimum dimension), or 5, but less than the maximum dimension of the red blood cell. Such embodiment has certain advantages in blood cell counting. In one embodiment, for red blood cell counting, by making the inner surface spacing at 2 or 6 µm and any number between the two values, an undiluted whole blood sample is confined in the spacing; on average, each red blood cell (RBC) does not overlap with others, allowing an accurate counting of the red blood cells visually. Too many overlaps between the RBC's can cause serious errors in counting.

For example, the white blood cell has a dimension of 5 um to 20 um. In an embodiment of the present invention, the spacers in one spacer height area are selected to make the inner surface spacing of the plates in a relevant area, for example, 5 µm (equal to the minimum dimension), 10 µm, or 30 (50% larger than the minimum dimension), or 5, but less than the maximum dimension of the white blood cell. Such embodiment has certain advantages in blood cell counting. In one embodiment, for white blood cell counting, by making the inner surface spacing at 5 or 30 µm and any number between the two values, an undiluted whole blood sample is confined in the spacing, allowing an accurate counting of the red blood cells visually.

In some embodiments, the spacer height, the spacing between the plates, and/or sample thickness in one spacer height area is: (i) equal to or smaller than the minimum dimension of an analyte, or (ii) equal to or slightly smaller than the maximum dimension of an analyte. The "slightly smaller" means that it is about 1% to 5% smaller and any number between the two values.

In some embodiments, the spacer height, the spacing between the plates, and/or sample thickness in one spacer height area is larger than the minimum dimension of an analyte (e.g., an analyte has an anisotropic shape), but less than the maximum dimension of the analyte.

In some embodiments, the plates and the spacers in one spacer height area are used to regulate not only the thickness of a sample, but also the orientation and/or surface density of the analytes/entity in the sample when the plates are at the closed configuration. When the plates are at a closed configuration, a thinner thickness of the sample results in less analytes/entity per surface area (i.e., less surface concentration).

The spacers can be a single spacer or a plurality of spacers on the plate or in a relevant area of the sample. In some embodiments, the spacers on the plates are configured and/or arranged in an array form, and the array is a periodic, non-periodic array or periodic in some locations of the plate while non-periodic in other locations.

In some embodiments, the periodic array of the spacers is arranged as lattices of square, rectangle, triangle, hexagon, polygon, or any combinations of thereof, where a combination means that different locations of a plate has different spacer lattices.

In some embodiments, the inter-spacer distance of a spacer array in one spacer height area is periodic (i.e. uniform inter-spacer distance) in at least one direction of the array. In some embodiments, the inter-spacer distance is configured to improve the uniformity between the plate spacing at a closed configuration.

In some embodiments, the distance between neighboring spacers (i.e. the inter-spacer distance) in one spacer height area is 1 μm or less, 5 μm or less, 7 μm or less, 10 μm or less, 20 μm or less, 30 μm or less, 40 μm or less, 50 μm or less, 60 μm or less, 70 μm or less, 80 μm or less, 90 μm or less, 100 μm or less, 200 μm or less, 300 μm or less, 400 μm or less, or in a range between any two of the values.

In certain embodiments, the inter-spacer distance in one spacer height area is at 400 μm or less, 500 μm or less, 1 mm or less, 2 mm or less, 3 mm or less, 5 mm or less, 7 mm or less, 10 mm or less, or in any range between the values. In certain embodiments, the inter-spacer distance is a 10 mm or less, 20 mm or less, 30 mm or less, 50 mm or less, 70 mm or less, 100 mm or less, or in any range between the values.

The distance between neighboring spacers (i.e. the inter-spacer distance) in one spacer height area is selected so that for a given properties of the plates and a sample, at the closed-configuration of the plates, the sample thickness variation between two neighboring spacers is, in some embodiments, at most 0.5%, 1%, 5%, 10%, 20%, 30%, 50%, 80%, or in any range between the values; or in certain embodiments, at most 80%, 100%, 200%, 400%, or in a range between any two of the values.

Clearly, for maintaining a given sample thickness variation between two neighboring spacers, when a more flexible plate is used, a closer inter-spacer distance is needed.

In a preferred embodiment, the inter-spacer spacing in one spacer height area is between 20 um and 50 um.

In a preferred embodiment, the inter-spacer spacing in one spacer height area is between 50 um and 80 um.

In a preferred embodiment, the inter-spacer spacing in one spacer height area is between 80 um and 100 um.

In a preferred embodiment, the inter-spacer spacing in one spacer height area is between 100 um and 150 um.

In a preferred embodiment, the inter-spacer spacing in one spacer height area is between 150 um and 200 um.

In a preferred embodiment, the inter-spacer spacing in one spacer height area is between 200 um and 250 um.

In a preferred embodiment, the inter-spacer spacing in one spacer height area is between 250 um and 300 um.

In a preferred embodiment, the inter-spacer spacing in one spacer height area is between 300 um and 400 um.

In a preferred embodiment, the inter-spacer spacing in one spacer height area is between 400 um and 500 um.

In a preferred embodiment, the spacer is a periodic square array, wherein the spacer in one spacer height area is a pillar that has a height of 2 to 6 μm, an average lateral dimension of from 10 to 40 μm, and inter-spacer spacing of 1 μm to 100 μm.

In a preferred embodiment, the spacer is a periodic square array, wherein the spacer in one spacer height area is a pillar that has a height of 2 to 6 μm, an average lateral dimension of from 10 to 50 μm, and inter-spacer spacing of 100 μm to 250 μm.

In a preferred embodiment, the spacer is a periodic square array, wherein the spacer in one spacer height area is a pillar that has a height of 10 to 50 μm, an average lateral dimension of from 20 to 50 μm, and inter-spacer spacing of 1 μm to 100 μm.

In a preferred embodiment, the spacer is a periodic square array, wherein the spacer in one spacer height area is a pillar that has a height of 10 to 50 μm, an average lateral dimension of from 20 to 50 μm, and inter-spacer spacing of 100 μm to 250 μm.

The period of spacer array in one spacer height area is between 1 nm to 100 nm in one preferred embodiment, 100 nm to 500 nm in another preferred embodiment, 500 nm to 1000 nm in a separate preferred embodiment, 1 μm (i.e. 1000 nm) to 2 μm in another preferred embodiment, 2 μm to 3 μm in a separate preferred embodiment, 3 μm to 5 μm in another preferred embodiment, 5 μm to 10 μm in a separate preferred embodiment, and 10 μm to 50 μm in another preferred embodiment, 50 μm to 100 μm in a separate preferred embodiment, 100 μm to 175 μm in a separate preferred embodiment, and 175 μm to 300 μm in a separate preferred embodiment.

The spacers in one spacer height area are arranged on the respective plates at a surface density of greater than one per $\mu m^2$, greater than one per 10 $\mu m^2$, greater than one per 100 $\mu m^2$, greater than one per 500 $\mu m^2$, greater than one per 1000 $\mu m^2$, greater than one per 5000 $\mu m^2$, greater than one per 0.01 $mm^2$, greater than one per 0.1 $mm^2$, greater than one per 1 $mm^2$, greater than one per 5 $mm^2$, greater than one per 10 $mm^2$, greater than one per 100 $mm^2$, greater than one per 1000 $mm^2$, greater than one per 10000 $mm^2$, or in a range between any two of the values. In some embodiments, the spacers have a density of at least $1/mm^2$, at least $10/mm^2$, at least $50/mm^2$, at least $100/mm^2$, at least $1,000/mm^2$, or at least $10,000/mm^2$.

Spacer area filling factor is defined as the ratio of spacer area to the total plate area or the ratio of spacer period to the width. In some embodiments, the filling factor is at least 1%, 2%, 3%, 4%, 5%, 6%, 7%, 8%, 9%, 10%, 20%, or in the range between any of the two values. In certain embodiments, the filling factor is at least 2.3%.

The device comprises two plates and spacers, wherein the fourth power of the inter-spacer-distance (ISD) divided by the thickness (h) and the Young's modulus (E) of the flexible plate (ISD^4/(hE) is 5×10^6 um^3/GPa or less.

The device comprises two plates and spacers, wherein the fourth power of the inter-spacer-distance (ISD) divided by the thickness (h) and the Young's modulus (E) of the flexible plate (ISD^4/(hE)) is 5×10^5 um3/GPa or less.

The device that comprises two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The device that comprises two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD^4/(hE)) is 5×10^6 um^3/GPa or less.

The device that comprises two plates and spacers, wherein the ratio of the inter-spacing distance of the spacers to the average width of the spacer is 2 or larger, and the filling factor of the spacers multiplied by the Young's modulus of the spacers is 2 MPa or larger.

In some embodiment, spacers in each sample area are used as the reference area for an optical signal during the measurement.

In some embodiment, spacers in each sample area are used as the reference area for the image correction standard during the measurement.

In some embodiment, the distance between the first measurement area with spacing height −1 and the second measurement area with spacing height −2 is larger than √Dt, wherein a D is the analyte diffusion coefficient of target analyte and t is the measurement time.

Example—1 Multi Height Spacing Device Measure Complete Blood Count

Figure 5:
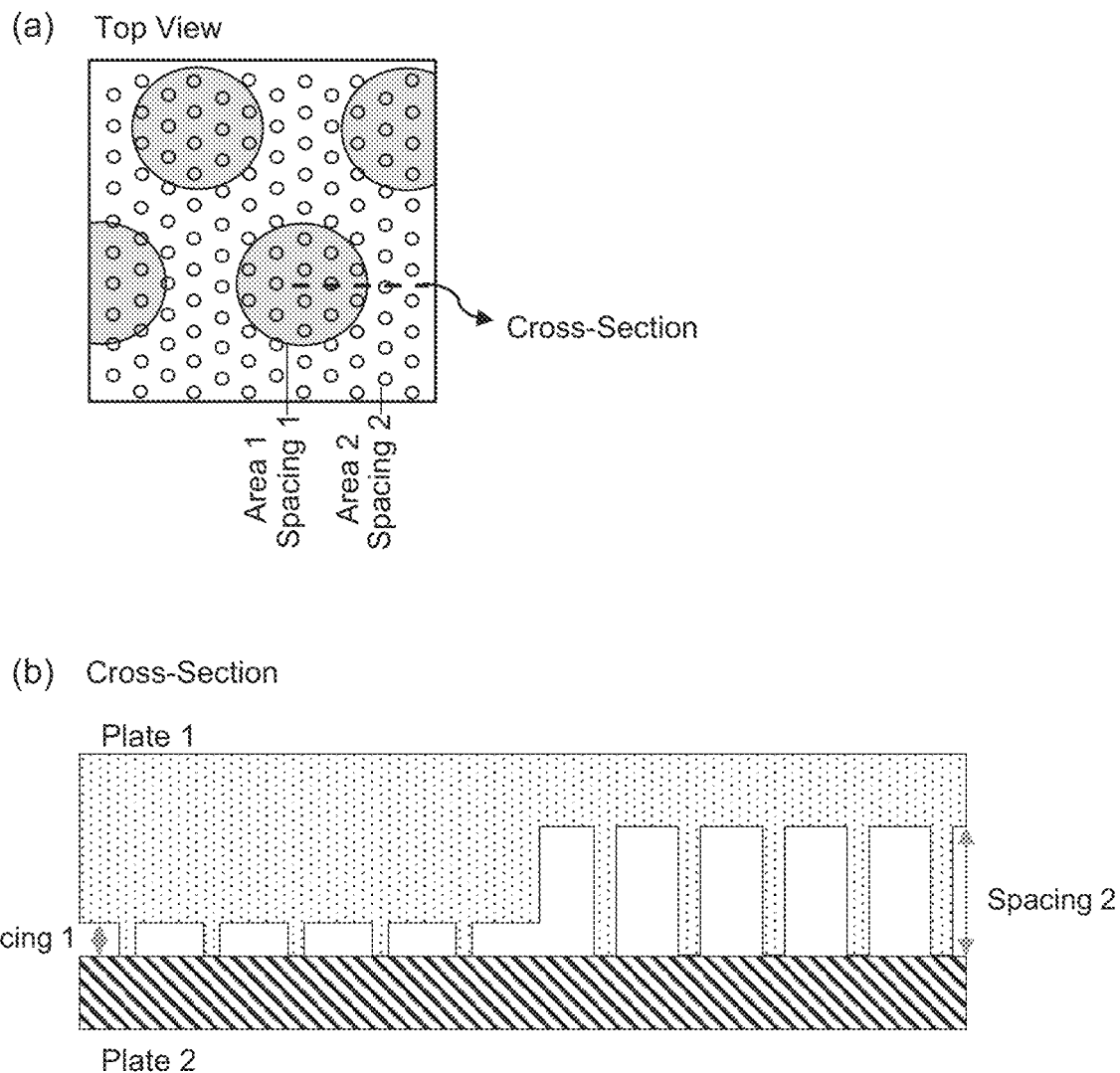
FIG. 5 shows one example device and method using multi spacing QMAX device to measure complete blood count (CBC).

One example device and method using multi spacing QMAX device to measure complete blood count (CBC) is shown in FIG. 5. The device is able to measure all the CBC parameters in one device without dilution. The preliminary test shows the results using such device is accurate compared with commercial machine.

FIG. 5 shows one example device and method using multi spacing QMAX device to measure complete blood count (CBC).

The device was fabricated with the materials of PMMA. The device can be fabricated with the materials of polystyrene, PMMA, PC, COC, COP, or another plastic.

The plate 1 used in the example has a thickness of 950 um to 1050 um. The plate 1 have a preferred thickness range of 200 um to 1500 um.

The plate 2 used in the example has a thickness of 170 um to 180 um. The plate 2 have a preferred thickness range of 50 um to 250 um.

The area 1 with pillar 1 array on the plate 2 in the experiment has a pillar height 5 um, inter pillar distance of 90 um, and a pillar size 20 um. The pillar can have a pillar height from 2 um to 6 um with an inter pillar distance of 50 um to 200 um and a pillar size 5 um to 40 um.

The area 2 with pillar 2 array on the plate 2 in the experiment has a pillar height 30 um, inter pillar distance of 80 um, and a pillar size 30 um. The pillar can have a pillar height from 20 um to 50 um with an inter pillar distance of 50 um to 200 um and a pillar size 10 um to 50 um.

The area 1 is a circle with a size of 0.77 mm in diameter and in a hexagonal lattice with a period of 1.21 mm. The area 1 and 2 have an area size range of 0.2 $mm^2$ to 2 $mm^2$. The area 1 and 2 has a periodicity range of 1 mm to 3 mm.

The size of each area and period of each area are designed to make sure each field of view in current optical system (around 3 mm by 3 mm) can have information of both areas.

In this experiment, the area 1 is designed into a circle not rectangular, since we observed cell is easily aggregated in the perpendicular corner of rectangle, thus not uniform distributed.

The acridine orange dye for staining WBC and PLT, and the Zwittergent for distribute the RBC is coated on the plate 1.

The acridine orange is coated on the plate with an area concentration of 1 to 20 $ng/mm^2$ and Zwittergent is coated on the plate with an area concentration of 1 to 30 $ng/mm^2$.

In some other examples, the staining reagent is coated on one of the plate or both plates. The cell separation reagent is coated on one of the plate or both plates. The cell lysing reagent is coated on one of the plate or both plates.

In some other examples, the cell stain agent comprises Wright's stain (Eosin, methylene blue), Giemsa stain (Eosin, methylene blue, and Azure B), May-Grünwald stain, Leishman's stain ("Polychromed" methylene blue (i.e. demethylated into various azures) and eosin), Erythrosine B stain (Erythrosin B), and other fluorescence stain including but not limit to Acridine orange dye, 3,3-dihexyloxacarbocyanine (DiOC6), Propidium Iodide (PI), Fluorescein Isothiocyanate (FITC) and Basic Orange 21 (BO21) dye, Ethidium Bromide, Brilliant Sulfaflavine and a Stilbene Disulfonic Acid derivative, Erythrosine B or trypan blue, Hoechst 33342, Trihydrochloride, Trihydrate, or DAPI (4',6-Diamidino-2-Phenylindole, Dihydrochloride), or any combinations thereof. In some embodiments, the cell separation agent comprises surfactant, Zwittergent, CHAPS, IIb, IIc, IId, CTAC, Tween 20, Tween 40, Tween 60, Tween 80, SLS, CTAB, or any combinations thereof. In some embodiments, the cell lysing agent comprises ammonium chloride, sodium bicarbonate, ethylenediaminetetraacetic acid (EDTA), acetic acid, citric acid, or other acid and base, or any combinations thereof.

When measuring and analyzing whole blood sample using such device, comprising following steps:

(a) obtaining a whole blood sample (can be finger prick fresh blood or $K_2$EDTA venous whole blood) and a device;

(b) depositing the sample on one or both of the plates when the plates are configured in the open configuration, (c) after (b), forcing the two plates into a closed configuration; and (d) illuminating the light on the device and capturing images of sample in the device while the plates are the closed configuration; and (e) analyzing the images to analyze complete blood count in the device.

Figure 6:
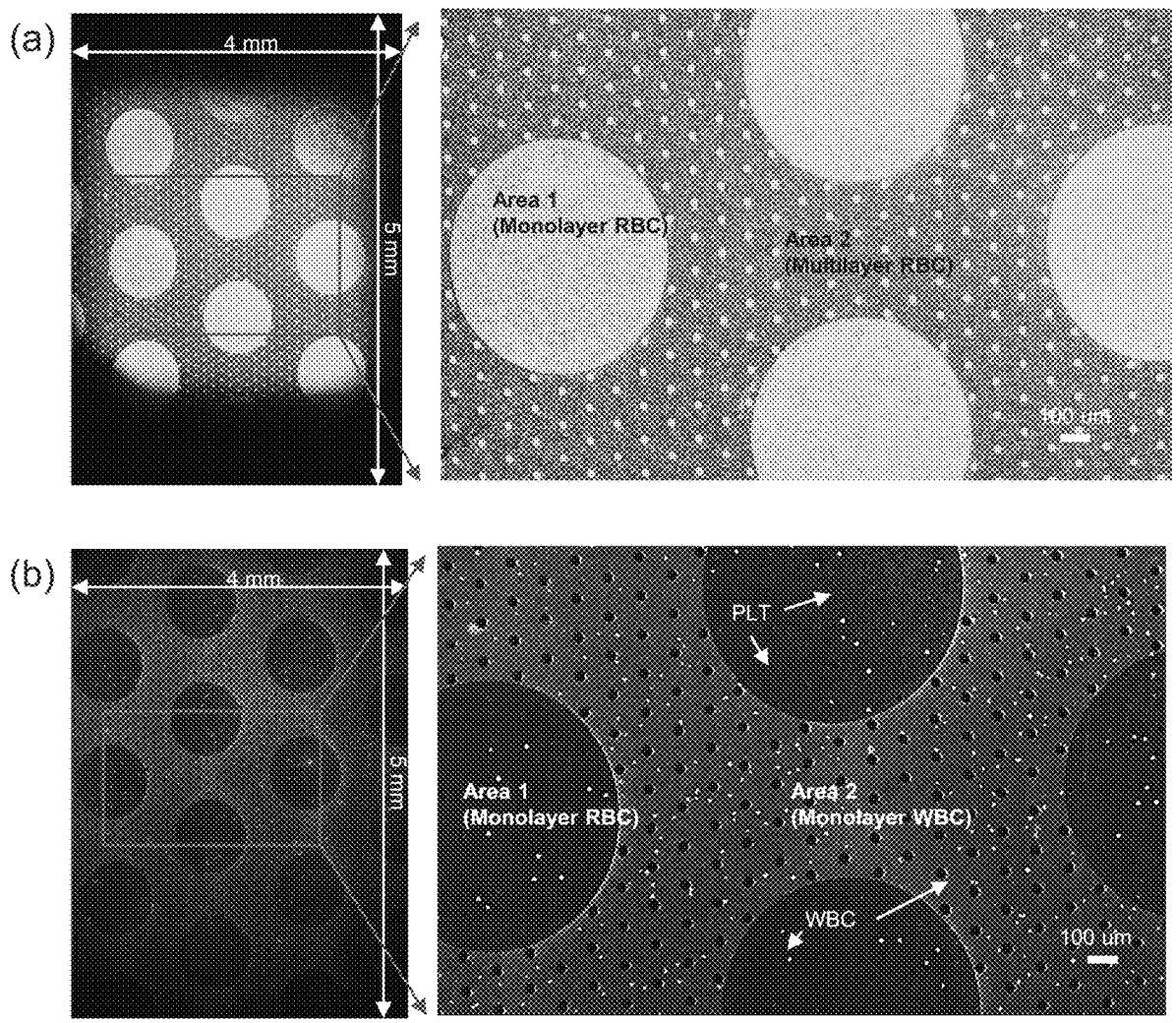
FIG. 6 shows (a) the bright field and (b) fluoresce field image of one example embodiment device with whole blood inside taken by iPhone based optical system.

FIG. 6 shows (a) the bright field and (b) fluoresce field image of one example embodiment device with whole blood inside taken by iPhone based optical system.

The red blood cell in area-1 with a pillar height 5 um become a monolayer and countable in the zoom-in image. The red blood cell in area-2 with pillar height 30 um become multilayers, thus good for HgB measurement.

The white blood cell and platelet is stained with AO dye and is bright dots in the fluorescence image. The white blood cell in both area-1 and area-2 become a monolayer and countable in the zoom-in image. The platelet in area 1 is a monolayer and countable in the zoom-in image.

During the HgB measurement in area-2, the optical transmittance at spacer region is used as the local optical reference for such measurement.

During the all the cell counting in area-1 and 2, the location, period and size of all the spacers are used as the local dimension correction marker for such measurement.

Whole blood samples (venous in $K_2$EDTA tube) from 8 patients are measured by multi height spacing device and compared with commercial hemocytometer as Horiba Pentra 60C. 6 uL whole blood was dropped onto plate 2, and pressed by plate 1. The card is then read by smartphone based optical system. The cells are counted by local software using both OpenCV and machine learning algorithm.

Figure 7:
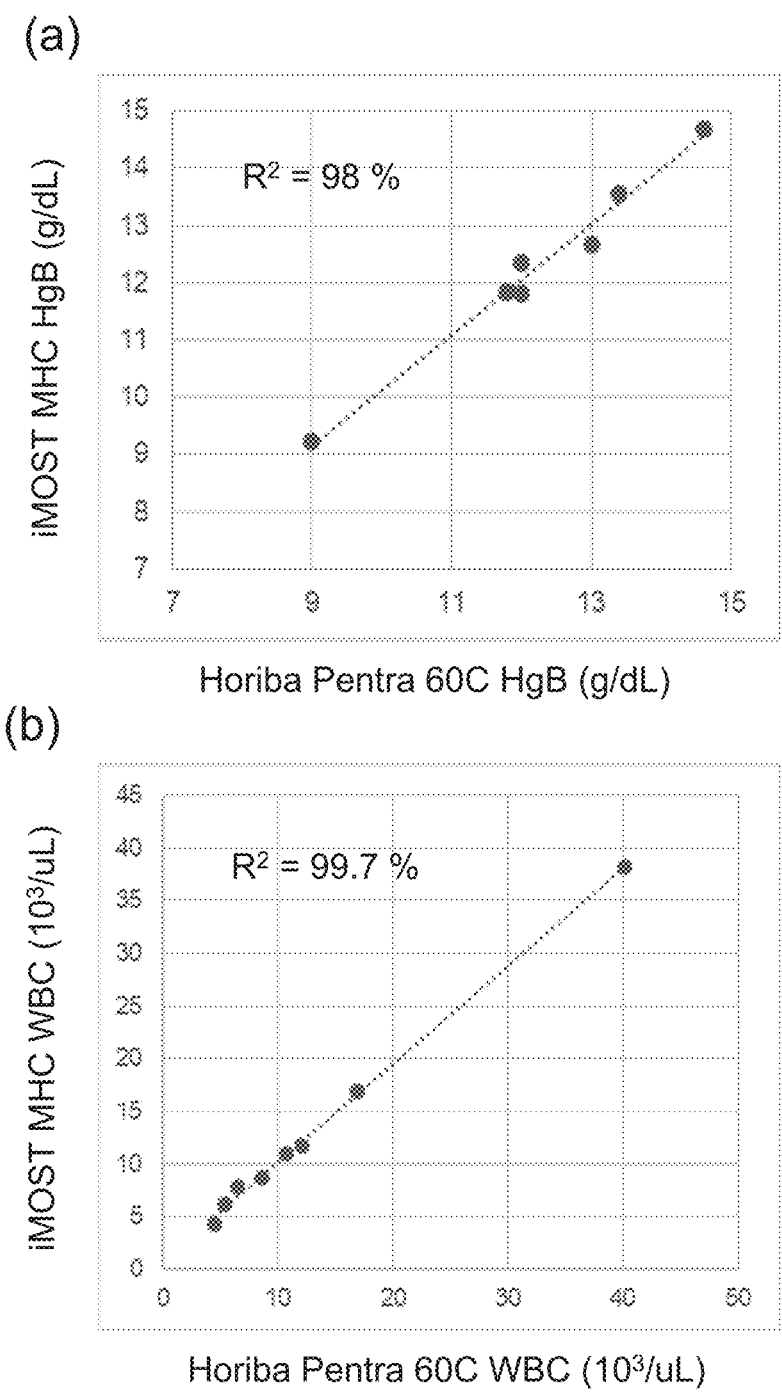
FIG. 7 shows the example HgB and WBC analyze results of whole blood samples using multi height card device and compared with commercial hemocytometer as Horiba Pentra 60C. The results show good accuracy of the device and method with R2 over 98% compared with commercial machine.

FIG. 7 shows the example HgB and WBC analyze results of whole blood samples using multi height card device and compared with commercial hemocytometer as Horiba Pentra 60C. The results show good accuracy of the device and method with R2 over 98% compared with commercial machine.

In details, compared with Horiba Pentra 60C, the HgB reading has R2=98% with commercial machine over measured range of 9 g/dL to 15 g/dL, while the WBC reading has R2=99.7% with commercial machine over measured range of $3\times10^3$/uL to $40\times10^3$/uL.

In the area of example device for WBC and HgB analysis:
1) Each area has a size around 0.5 mm$^2$ to 4 mm$^2$.
2) The area is rectangular or hexagonal arranged with a periodicity of 1 mm to 3 mm.
3) The spacer height, the spacing between the plates, and/or sample thickness is around 30 um.
4) The spacer height, the spacing between the plates, and/or sample thickness is 20 um to 40 um.
5) The spacer is rectangle shape with round corners.
6) The lateral dimension of a spacer is around 30 μm by 40 um.
7) The lateral dimension of a spacer is 10 um to 40 um.
8) The round corners of spacer has a diameter of 10 um.
9) The spacer is in a rectangular lattice array.
10) The inter-spacer spacing of spacers is around 80 μm.
11) The inter-spacer spacing of spacers is 70 μm to 150 um.
12) The reagent is coated by droplet printing into an array.
13) The reagent is coated by spray.
14) The acridine orange or other staining reagents is coated onto the first plate, or the second plate or both.
15) The Zwittergent or other detergent is coated onto the first plate, or the second plate or both.
16) The acridine orange is coated on the plate with an area concentration of 5 to 20 ng/mm$^2$ and Zwittergent is coated on the plate with an area concentration of 10 to 30 ng/mm$^2$.
17) The material of first place and second plate is Poly (methyl methacrylate).

In the area of embodiment device for RBC and PLT analyze:
1) Same as above, except:
2) The spacer height, the spacing between the plates, and/or sample thickness is around 5 um.
3) The spacer height, the spacing between the plates, and/or sample thickness is 2 um to 7 um.
4) The lateral dimension of a spacer is around 30 μm by 40 um.
5) The lateral dimension of a spacer is 5 um to 40 um.
6) The acridine orange or other staining reagents is coated onto the first plate, or the second plate or both.
7) The Zwittergent or other detergent is coated onto the first plate, or the second plate or both.
8) The acridine orange is coated on the plate with an area concentration of 10 to 80 ng/mm$^2$ and Zwittergent is coated on the plate with an area concentration of 20 to 120 ng/mm$^2$.

A-2. Reducing Hook Effects Using QMAX-Card with Different Spacer Height

In the present invention, in some embodiments, the Hook Effect in an assay is reduced by using the QMAX card with different spacer height. The reason is that (a) the QMAX device (also called card) the large area to the sample thickness ratio makes the lateral diffusion of analyte negligible compared to assay reaction time and (b) the total analyte/interference per unit area in a sample is proportional to the sample thickness, hence reducing the sample thickness (determined by the local spacer height) reduces the Hook effect.

In some embodiments, a device for reducing the Hook effect in an assay comprises a QMAX device of any embodiment that has at least two areas, each area having a different spacer height.

In some embodiments, a device for increasing the dynamic range in an assay comprises a QMAX device of any embodiment that has at least two areas, each area having a different spacer height.

In some embodiments, a device for reducing the Hook effect, comprises a QMAX device of any embodiment that has at least two areas, each area having a different spacer height, wherein the inner surface of the plate in each area has a coating of a reagent.

In some embodiments, a device for increasing the dynamic range, comprises a QMAX device of any embodiment that has at least two areas, each area having a different spacer height, wherein the inner surface of the plate in each area has a coating of a reagent.

In some embodiments, the reagents coated in each different spacer height area have the same concentrations. In some embodiments, the reagents coated in each different spacer height area have a different concentration.

In some embodiments, the disclosure provides a method for reducing the Hook effect in an assay comprising:
(a) obtaining a sample containing or is suspected of containing a target analyte;
(b) obtaining a device of any embodiment having a QMAX device comprising two or more different spacer height areas;
(c) depositing the sample on one or both of the plates when the plates are in the open configuration,
(d) after (c), bringing the two plates together and pressing the plates into a closed configuration,
(e) after (d), measuring the sample using imaging,
wherein the sample is measured in at least two different spacer height areas.

In some embodiments, the assay in the lower spacer height area measures higher concentration of analyte, and the assay in the higher spacer height area measures lower concentration of analyte.

In some embodiments, the spacer height in one spacer height area is 3 nm or less, 10 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, 500 µm or less, 800 µm or less, 1 mm or less, 2 mm or less, 4 mm or less, or in a range between any two of the values.

In some embodiments, the preferred spacer height in one spacer height area is 2 µm or less, 3 µm or less, 5 µm or less, 10 µm or less, 20 µm or less, 30 µm or less, 50 µm or less, or in a range between any two of the values.

In some embodiments, the concentration of coated antibody in one spacer height area is 1 ng/mL or less, 3 ng/mL or less, 5 ng/mL or less, 10 ng/mL or less, 30 ng/mL or less, 50 ng/mL or less, 100 ng/mL or less, 500 ng/mL or less, 1 ug/mL or less, 5 ug/mL or less, 10 ug/mL or less, 20 ug/mL or less, 50 ug/mL or less, 100 ug/mL or less, or in a range between any two of the values.

In some embodiments, the preferred concentration of coated antibody in one spacer height area is 1 ng/mL or less, 3 ng/mL or less, 5 ng/mL or less, 10 ng/mL or less, 30 ng/mL or less, 50 ng/mL or less, 100 ng/mL or less, 500 ng/mL or less, 1 ug/mL or less, 5 ug/mL or less, 10 ug/mL or less, 20 ug/mL or less, 50 ug/mL or less, 100 ug/mL or less, or in a range between any two of the values.

In some embodiments, the size of beads in one spacer height area is 3 nm or less, 10 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, 500 µm or less, 800 µm or less, 1 mm or less, 2 mm or less, 4 mm or less, or in a range between any two of the values.

In some embodiments, the size of beads in one spacer height area 2 µm or less, 3 µm or less, 5 µm or less, 10 µm or less, 20 µm or less, 30 µm or less, 50 µm or less or in a range between any two of the values.

Example—2 Multi Height Spacing Device Measure C-Reactive Protein (CRP)

A device for analyzing C-Reactive Protein (CRP) in a blood sample, comprising: a first plate, a second plate, spacers, and adaptor wherein:
i. the plates are movable relative to each other into different configurations;
ii. one or both plates are flexible;
iii. each of the plates comprises an inner surface that has a sample contact area for contacting a fluidic sample;
iv. one or both of the plates comprise the spacers that are permanently fixed on the sample contact area of a respective plate;
v. one or both of the plates has at least two areas, each has a different spacer height.
vi. the sample contact area includes at least two different spacer height areas.
vii. one or both of the plates comprise the reagents that are coated on the sample contact area of a respective plate;
viii. the reagents have at least one of the following: (a) a component of solid surface (particles) to capture CRP; (b) a component to detect CRP; and (c) a component to stabilize all reagents;
ix. the adaptor comprises: (a) a housing, (b) an attachment member on the housing that allows the adaptor to be attached to a mobile phone with a camera, (c) a slot in the housing that allows (1) the plates in a closed configuration to slide into the slot and (2) when the plates are in the slot, at least a part of the sample area is less than 2 cm away from the outer surface of the camera, and (d) an optical system in the housing configured to have at least a part of the sample contact area be imaged by the camera;
wherein one of the configurations is an open configuration, in which: the two plates are partially or completely separated apart, the spacing between the plates is not regulated by the spacers, and the sample is deposited on one or both of the plates;
wherein another of the configurations is a closed configuration which is configured after the sample is deposited in the open configuration; and in the closed configuration: at least part of the sample is compressed by the two plates into a layer of highly uniform thickness in each area with different spacer height and is substantially stagnant relative to the plates, wherein the uniform thickness of the layer is confined by the sample contact areas of the two plates and is regulated by the plates and the spacers.

Figure 8:
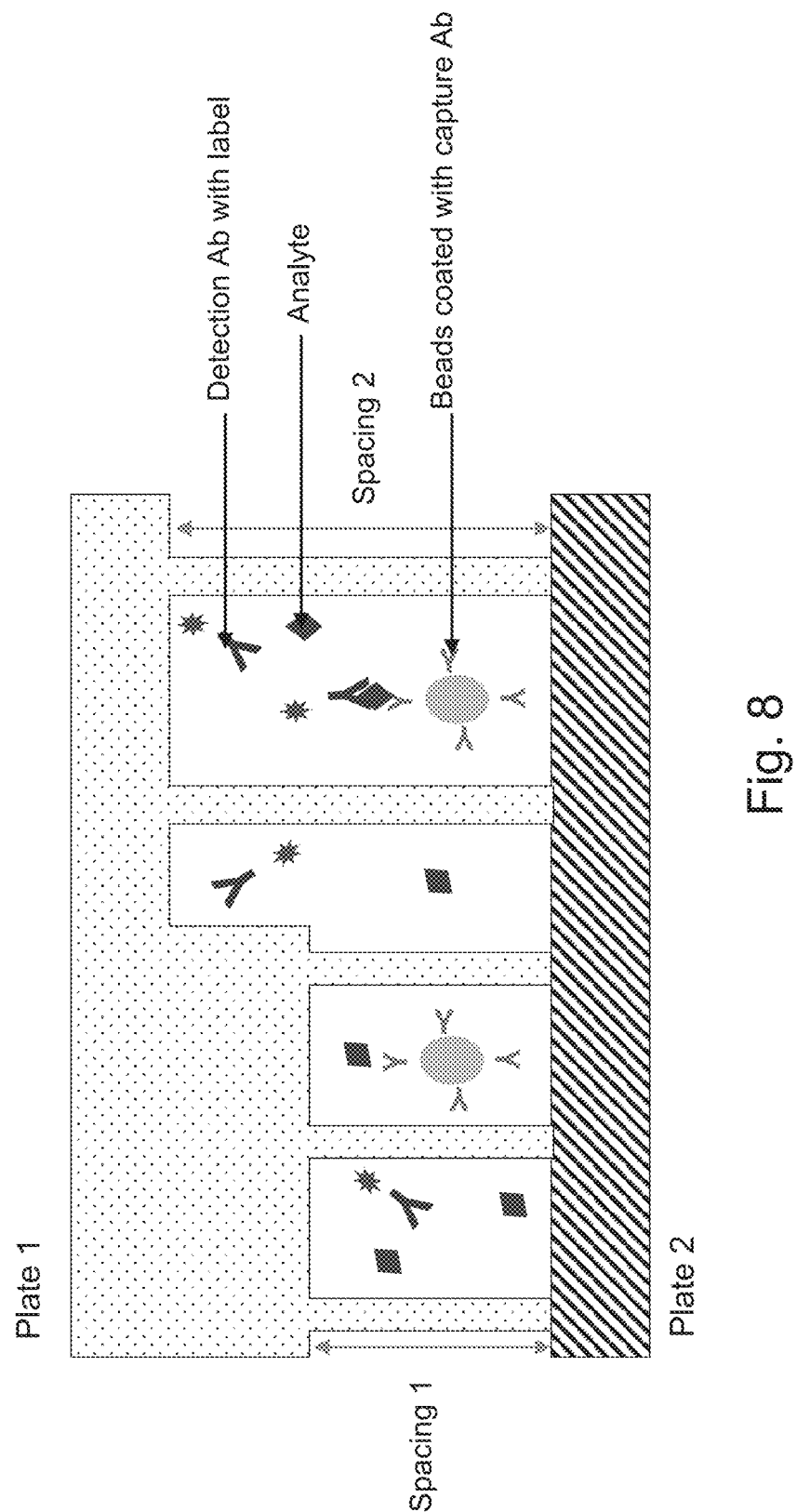
FIG. 8 shows one example device and method using multi spacing QMAX device to measure antigen as C-Reactive Protein (CRP) using sandwich immunoassay.

One example device and method using multi spacing QMAX device to measure antigen as C-Reactive Protein (CRP) using sandwich immunoassay is shown in FIG. 8. The experiment achieved CRP measurement in multi height spacing without washing within 1 minute. It potentially can solve the hook effect, enlarge the dynamic range and increase the accuracy of such measurement.

The device was fabricated with the materials of PMMA. The device can be fabricated with the materials of polystyrene, PMMA, PC, COC, COP, or another plastic.

The plate 1 used in the example has a thickness of 950 um to 1050 um. The plate 1 can have a thickness of 200 um to 1500 um.

The plate 2 used in the example has a thickness of 170 um to 180 um. The plate 2 can have a thickness of 50 um to 250 um.

The area 1 with pillar 1 array on the plate 2 in the experiment has a pillar height 5 um, inter pillar distance of 90 um, and a pillar size 20 um. The pillar can have a pillar height from 2 um to 6 um with an inter pillar distance of 50 um to 200 um and a pillar size 5 um to 40 um.

The area 2 with pillar 2 array on the plate 2 in the experiment has a pillar height 30 um, inter pillar distance of 80 um, and a pillar size 30 um. The pillar can have a pillar height from 20 um to 50 um with an inter pillar distance of 50 um to 200 um and a pillar size 10 um to 50 um.

The area 1 is a circle with a size of 0.77 mm in diameter and in a hexagonal lattice with a period of 1.21 mm. The area 1 and 2 have an area size range of 0.2 mm$^2$ to 2 mm$^2$. The area 1 and 2 has a periodicity range of 1 mm to 3 mm.

The detection reagent as detection antibody with label is coated on one of the plate or both plates. In this experiment, the detection reagent is Cy5-labeled anti-CRP mouse monoclonal detection antibody with a concentration of 20 ug/mL. The preferred concentration range is 1 ug/mL to 50 ug/mL.

The capture reagent as capture antibody is coated on beads between both plates. In this experiment, the capture reagent is anti-CRP mouse monoclonal capture antibody. The beads have a size of 4.5 um to 5.5 um. The preferred beads size is 1 um, 2 um, 3 um, 5 um, 10 um, 20 um, 50 um of a size between any of these two values.

A method for measuring and analyzing C-Reactive Protein (CRP) using such device, comprising:
 (a) Conjugation of capture antibody to beads. COOH activated polystyrene beads (ThermoFisher, 5 μm in diameter) were conjugated to anti-CRP mouse monoclonal capture antibody (Fitzgerald).
 (b) Blocking of beads. The antibody conjugated beads were blocked by 4% BSA in PBS at 4° C. over night and washed by PBST for 6 times prior to use.
 (c) Coating first and second plate. Beads from Step 2 were well vortexed and was printed on the X-plate with multi-height pillars of Essenlix QMAX card and air dried at room temperature. Cy5-labeled anti-CRP mouse monoclonal detection antibody (Fitzgerald) with concentration around 1 ug/mL to 50 ug/mL was printed on substrate card and air dried at room temperature.
 (d) Assay with multi height card. 3 μL of sample (CRP analyte (Fitzgerald) at various concentrations) was dropped onto the printed area on QMAX card. The QMAX card was immediately closed and sample with beads were incubated for 1 minute.
 (e) Imaging. Without washing, the fluorescent images were taken by iPhone 6s using laser illumination.

Figure 9:
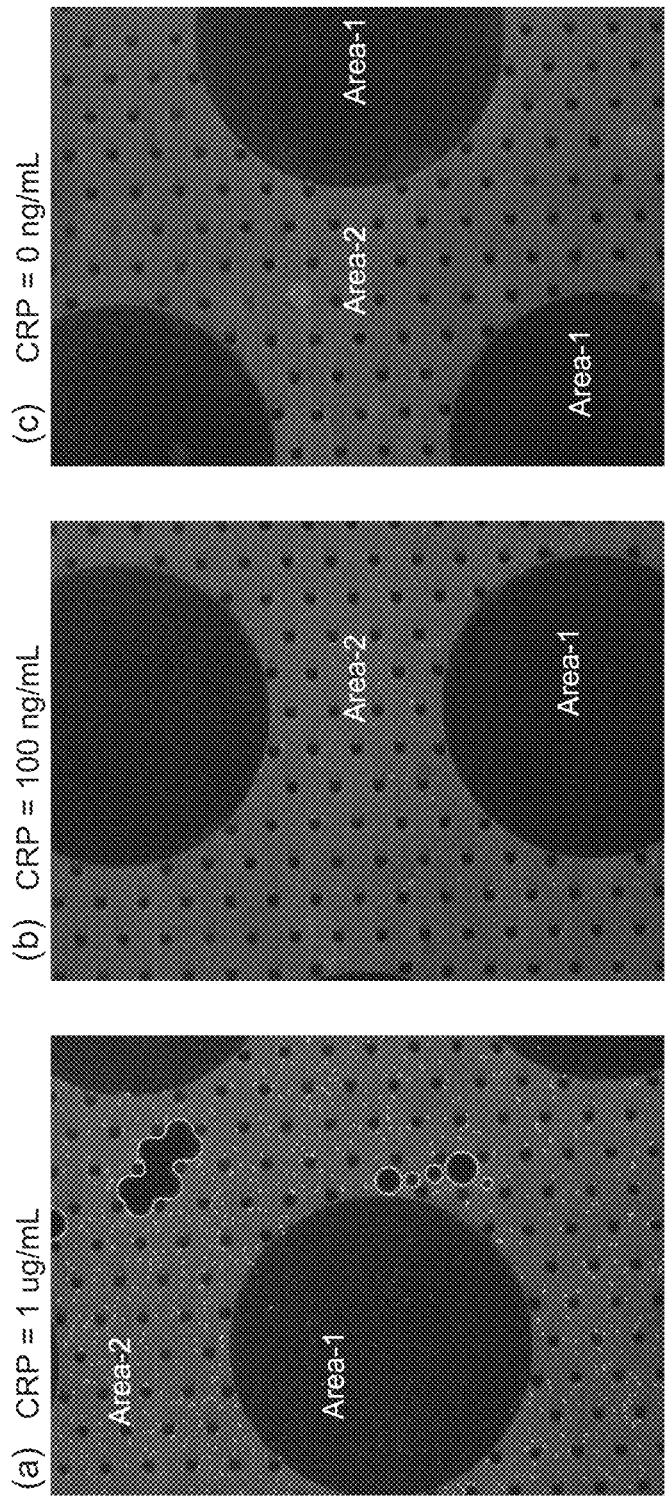
FIG. 9 shows fluoresce field image of one example embodiment device with different level of CRP (1 ug/mL, 100 ng/mL, 0 ng/mL) inside taken by iPhone. The device has two spacing area with 5 um spacing in area-1 and 30 um spacing in area 2.

FIG. 9 shows fluoresce field image of one example embodiment device with different level of CRP (1 ug/mL, 100 ng/mL, 0 ng/mL) inside taken by iPhone. The device has two spacing areas with 5 um spacing in area-1 and 30 um spacing in area 2.

Clearly (1) with same concentration of antigen (CRP), the beads in area 2 is brighter than area 1 due to larger spacing height in area 2, thus more capture volume. (2) with different level of antigen, the beads in both area 1 and 2 become brighter with higher concentration.

By comparing the signal of each area, following purpose can be achieved, (1) reducing the hook effect at very high concentration of CRP by measuring the CRP in low spacing height, (2) enlarge the dynamic range of CRP measurement, for example, use area 1 for high concentration of CRP, while area 2 for low concentration of CRP, (2) reducing the CRP measurement error by measuring same sample in different height in the same device to reduce the statistic error.

In some examples, the capture antibody can be applied to the surface or beads by printing, spraying, soaking or any other method that applies homogenous or partial layer of reagents.

In some examples, the capture antibody is either monoclonal, polyclonal antibody, engineered antibody (e.g., single chain variable fragments (scFv)) or fragments thereof. In some embodiments, the concentration of coated capture antibody ranges from 1 ng/mL to 1 mg/mL.

While antibodies can be used to detect antigens, antigens can also be used to detect antibodies.

In some embodiments the first plate comprises blockers that are coated on the inner surface of the first plate.

In some embodiments the first plate comprises a stabilizer that is coated on the inner surface of the first plate. In some embodiments, the stabilizer is sugar such as but not limited to sucrose and glucose. In some embodiments, the stabilizer is a polymer. In certain embodiments, the stabilizer is glycerol.

In some embodiments the second plate comprises a detection antibody that is coated on the inner surface of the second plate. In some embodiments, the detection antibody can be applied to the surface by printing, spraying, soaking or any other method that applies homogenous layer of reagents. In certain embodiments, the detection antibody is dried on the second plate. In some embodiments, the detection antibody is either monoclonal, polyclonal antibody, engineered antibody (e.g. single chain variable fragments (scFv)) or fragments thereof. In some embodiments, the concentration of coated detection antibody ranges from 100 ng/mL to 1 mg/mL.

In some embodiments, the detection antibody is configured to produce a detectable signal after binding to the analyte. For example, in some embodiments the signal can be a colorimetric signal, a luminescent signal, or a fluorescent signal. In some embodiments for example, the detection antibody is labeled by a fluorescent label, which produces a signal after the detection antibody binds to the analyte or to the capture antibody-analyte complex. In some embodiments, the fluorescent label directly labels the detection antibody. In some embodiments, the fluorescent label labels a reagent that can bind to the detection antibody or a detection antibody-analyte complex. In some embodiments, the secondary antibody can be conjugated with an optical detectable label, e.g., a fluorophore such as but not limited to cy5, IR800, SAPE IRDye800CW, Alexa 790, Dylight 800.

In some embodiments, the detection antibody is configured to a chemical that can amplified signal or the signal from this chemical can be amplified; wherein amplification method in this amplification step including, but not limit to:

The color based enzymatic reaction, the absorption signal generated by substrates are amplified by enzyme which are linked to the detection reagents; wherein the enzyme including horseradish peroxidase; wherein the substrates including ABTS or TMB;

The fluorescence based enzymatic reaction, the fluorescence signal generated by substrates are amplified by enzyme which are linked to the detection reagents; wherein the enzyme including horseradish peroxidase or β-galactosidase; wherein the substrates including Amplex red or Resorufin β-D-Galactopyranoside;

Example—3 Another Multi Height Spacing Device Measure Complete Blood Count

Figure 10:
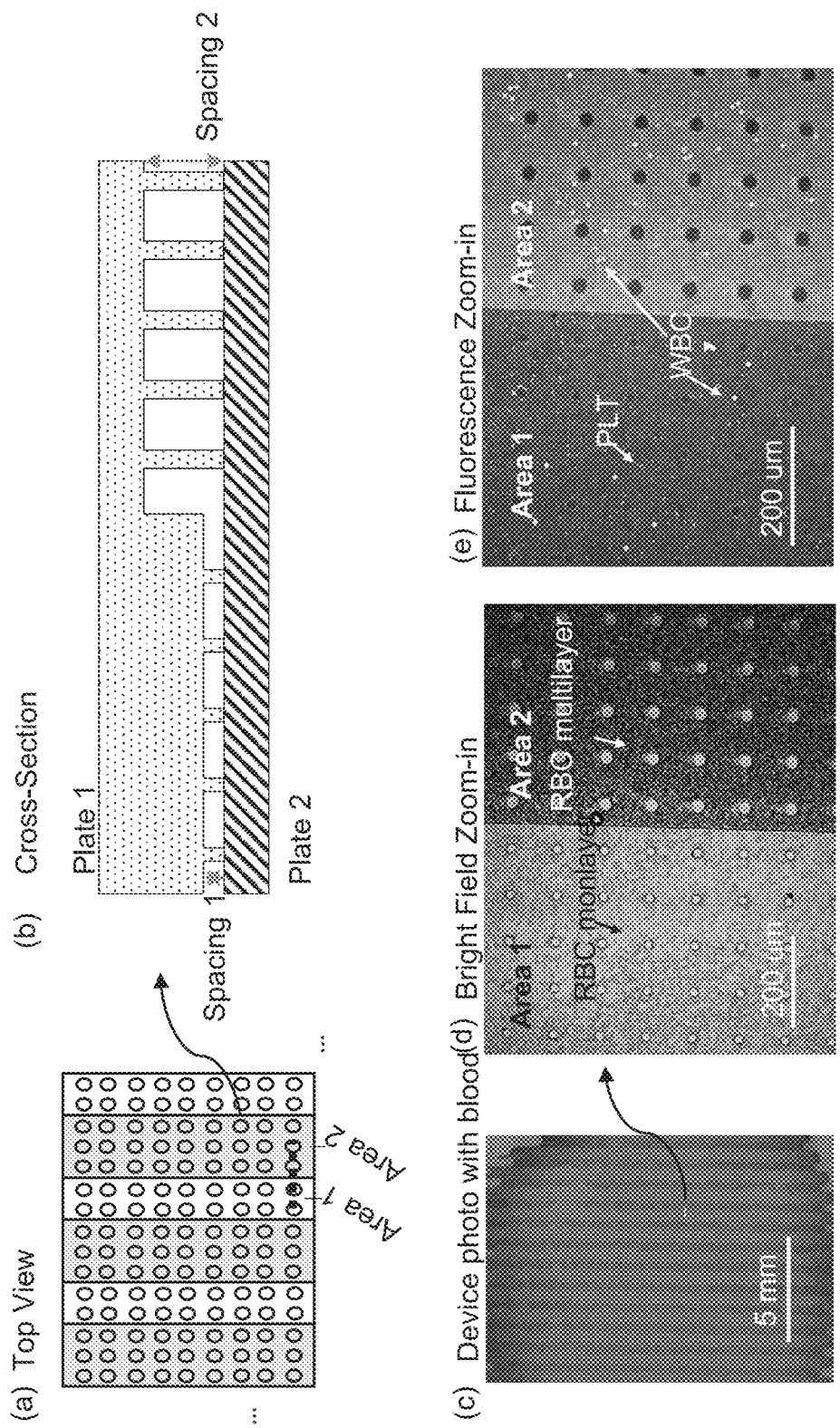
FIG. 10 shows an example of another device using multi spacing assay. (a) shows the top view and (b) shows the cross-section schematic of multi height array with 1D linear arrangement with spacing 1 and spacing 2. (c) shows one example photo of such device with un-diluted whole blood inside. The two spacing height is 5 um and 30 um. (d) shows the bright field photo of RBC monolayer in one spacing height and RBC multi layers in another spacing height. (e) shows the fluorescence field of PLT and WBC in both spacing height stained by nucleic acid staining.

Another example device and method using multi spacing QMAX device to measure complete blood count (CBC) is shown in FIG. 10. The device is able to measure all the CBC parameters in one device without dilution.

FIG. 10 shows an example of another device using multi spacing assay. (a) shows the top view and (b) shows the cross-section schematic of multi height array with 1D linear arrangement with spacing 1 and spacing 2. (c) shows one example photo of such device with un-diluted whole blood inside. The two spacing height is 5 um and 30 um. (d) shows the bright field photo of RBC monolayer in one spacing height and RBC multi layers in another spacing height. (e) shows the fluorescence field of PLT and WBC in both spacing height stained by nucleic acid staining.

The device was fabricated with the materials of PMMA. The device can be fabricated with the materials of polystyrene, PMMA, PC, COC, COP, or another plastic.

The plate 1 used in the example has a thickness of 950 um to 1050 um. The plate 1 have a preferred thickness range of 200 um to 1500 um.

The plate 2 used in the example has a thickness of 170 um to 180 um. The plate 2 have a preferred thickness range of 50 um to 250 um.

The area 1 with pillar 1 array on the plate 2 in the experiment has a pillar height 5 um, inter pillar distance of 90 um, and a pillar size 20 um. The pillar can have a pillar height from 2 um to 6 um with an inter pillar distance of 50 um to 200 um and a pillar size 5 um to 40 um.

The area 2 with pillar 2 array on the plate 2 in the experiment has a pillar height 30 um, inter pillar distance of 80 um, and a pillar size 30 um. The pillar can have a pillar height from 20 um to 50 um with an inter pillar distance of 50 um to 200 um and a pillar size 10 um to 50 um.

The area 1 and area 2 is arrange in 1D lattice with a period of 1.21 mm. The area 1 has a width of 0.66 mm, and the area 2 has a width of 0.55 um.

The preferred period of area 1 and 2 is 0.5 mm, 1.0 mm, 1.5 mm, 2 mm, 3 mm, 5 mm, 10 mm or a value between any of these.

The size of each area and period of each area are designed to make sure each field of view in current optical system (around 3 mm by 3 mm) can have information of both areas.

The acridine orange dye for staining WBC and PLT, and the Zwittergent for distribute the RBC is coated on the plate 1.

The acridine orange is coated on the plate with an area concentration of 1 to 20 ng/mm$^2$ and Zwittergent is coated on the plate with an area concentration of 1 to 30 ng/mm$^2$.

In some other examples, the staining reagent is coated on one of the plate or both plates. The cell separation reagent is coated on one of the plate or both plates. The cell lysing reagent is coated on one of the plate or both plates.

Similar to the experimental observation in Example 1, the red blood cell in area-1 with a pillar height 5 um become a monolayer and countable in the zoom-in image. The red blood cell in area-2 with pillar height 30 um become multilayers, thus good for HgB measurement.

The white blood cell and platelet is stained with AO dye and is bright dots in the fluorescence image. The white blood cell in both area-1 and area-2 become a monolayer and countable in the zoom-in image. The platelet in area 1 is a monolayer and countable in the zoom-in image.

The advantage of 1D arrangement in example 3 over example 1 is easier for software analyzing during the scanning applications.

A-3. Assaying Using QMAX Device with Different Spacer Height

In some embodiments, an assay is performed by using a QMAX device with different spacer height area, and by imaging the different spacer height area spatially and/or temporally. Such embodiments can offer additional information that is unavailable in the single spacer height assay.

The addition information includes, but not limited to, the effects of the concentration ratio of analyte to the reagent, the binding efficiency of the analyte to the reagent, the dynamic range of assay, the lower limit of detection of assay, the upper limit of detection of assay, the quantitative value of the testing analyte, the linearity of the assay, the kinetic performance of the assay, and the limit of quantification of the assay.

In some embodiments, a device for assaying an analyte in a sample, comprising a QMAX device of any embodiment that has at least two areas, each has a different spacer height, wherein the areas have a reagent coated on their surface, wherein the assaying the analyte comprises a step of comparing the information provided by an image from each different spacer height area.

In some embodiments, the reagents coated in each different spacer height area have the same concentrations. In some embodiments, the reagents coated in each different spacer height area have a different concentration.

In some embodiments, a method for assaying an analyte in a sample, comprising:

(a) obtaining a sample containing or suspected of containing a target analyte;

(b) obtaining a device of any embodiment of a QMAX device comprising two or more different spacer height areas;

(c) depositing the sample on one or both of the plates when the plates are in the open configuration, (d) after (c), bringing the two plates together and pressing the plates into a closed configuration, (e) after (d), measuring the sample using imaging, wherein the sample is measured in at least two different spacer height areas, wherein the assaying an analyte comprises a step of comparing the information provided by an image from each different spacer height area.

In some embodiments, the comparison of the information from two different spacer height comprises taking a ratio.

In some embodiments, the comparison of the information from two different spacer height comprises taking a subtraction.

In some embodiments, one analyte is assayed in at least two different spacer height areas.

In some embodiments, at least two analytes are assayed in at least two different spacer height areas.

In some embodiments, different spacer height area perform different measurements, which are different type of measurements (e.g., affinity assay, colorimetric assay, and/or nucleic acids) and/or different types of biomarkers (e.g., proteins, small molecules, cells, and nucleic acids), or any combination thereof.

In some embodiments, the spacer height in one spacer height area is 3 nm or less, 10 nm or less, 50 nm or less, 100 nm or less, 200 nm or less, 500 nm or less, 800 nm or less, 1000 nm or less, 1 μm or less, 2 μm or less, 3 μm or less, 5 μm or less, 10 μm or less, 20 μm or less, 30 μm or less, 50 μm or less, 100 μm or less, 150 μm or less, 200 μm or less, 300 μm or less, 500 μm or less, 800 μm or less, 1 mm or less, 2 mm or less, 4 mm or less, or in a range between any two of the values.

In some embodiments, the preferred spacer height in one spacer height area is 2 μm or less, 3 μm or less, 5 μm or less, 10 μm or less, 20 μm or less, 30 μm or less, 50 μm or less, or in a range between any two of the values.

In some embodiments, the concentration of coated antibody in one spacer height area is 1 ng/mL or less, 3 ng/mL or less, 5 ng/mL or less, 10 ng/mL or less, 30 ng/mL or less, 50 ng/mL or less, 100 ng/mL or less, 500 ng/mL or less, 1 ug/mL or less, 5 ug/mL or less, 10 ug/mL or less, 20 ug/mL or less, 50 ug/mL or less, 100 ug/mL or less, or in a range between any two of the values.

In some embodiments, the preferred concentration of coated antibody in one spacer height area is 1 ng/mL or less, 3 ng/mL or less, 5 ng/mL or less, 10 ng/mL or less, 30 ng/mL or less, 50 ng/mL or less, 100 ng/mL or less, 500 ng/mL or less, 1 ug/mL or less, 5 ug/mL or less, 10 ug/mL or less, 20 ug/mL or less, 50 ug/mL or less, 100 ug/mL or less, or in a range between any two of the values.

In some embodiments, the size of beads in one spacer height area is 3 nm or less, 10 nm or less, 50 nm or less, 100 nm or less, 200 nm or less, 500 nm or less, 800 nm or less, 1000 nm or less, 1 μm or less, 2 μm or less, 3 μm or less, 5 μm or less, 10 μm or less, 20 μm or less, 30 μm or less, 50 μm or less, 100 μm or less, 150 μm or less, 200 μm or less, 300 μm or less, 500 μm or less, 800 μm or less, 1 mm or less, 2 mm or less, 4 mm or less, or in a range between any two of the values.

In some embodiments, the size of beads in one spacer height area 2 μm or less, 3 μm or less, 5 μm or less, 10 μm or less, 20 μm or less, 30 μm or less, 50 μm or less, or in a range between any two of the values.

In some embodiments, a device for performing different biological and chemical tests, comprising a QMAX device of any embodiment that has at least two areas that each has a different spacer height, whereas one biological and chemical test is performed in one of the spacer height area, and another biological and chemical test is imaged in another spacer height area.

In some embodiments, a device for performing different functional tests, comprises a QMAX device of any embodiment that has at least two areas that each has a different spacer height, where one functional test is performed in one of the spacer height area, and another functional test is imaged in another spacer height area.

In some embodiments, a device for performing different biological and chemical tests, comprising a QMAX device of any embodiment that has at least two areas that each has a different plate type, whereas one biological and chemical test is performed in one type of plate area, and another biological and chemical test is imaged in another type of plate area.

In some embodiments, a device for performing different biological and chemical tests, comprises a QMAX device of any embodiment that has at least two areas that each has a different plate type, whereas one biological and chemical test is performed in one type of plate area, and another biological and chemical test is imaged in another type of plate area.

In some embodiments, the plate type in one area is the transparent plate with transparence at measurement wavelength range over 10%, 20%, 30%, 40%, 50%, 80%, 90%, or in a range between any of the two values.

In some embodiments, the plate type in one area is the non-transparent plate with reflectance at measurement wavelength range over 10%, 20%, 30%, 40%, 50%, 80%, 90%, or in a range between any of the two values.

In some embodiments, the plate type in one area is the white non-transparent plate with rough surfaces.

In some embodiments, a sample has its shape deformable but not self-flowable.

The biological, chemical, and functional tests in above embodiments, can include but are not limit to:

Blood cell tests, including but not limit to White blood cell count (WBC or leukocyte count), WBC differential count, Red blood cell count or erythrocyte count, Hematocrit (Hct), Hemoglobin (Hbg), Mean corpuscular volume (MCV), Mean corpuscular hemoglobin (MCH), Mean corpuscular hemoglobin concentration (MCHC), Red cell distribution width (RDW), Platelet count, Mean Platelet Volume (MPV);

Blood tests, including but not limit to blood glucose test, calcium blood test, cardiac enzyme test, cholesterol and lipid tests, C-reactive protein test, D-dimer test, erythrocyte sedimentation rate (ESR) test, Folate test, HbA1C test, HCG test, international normalized ratio (INR) test, iron studies, kidney function tests, liver function tests, magnesium blood test, oestrogen blood test, PSA test, testosterone blood test, thyroid function test, Vitamin B12 test, Vitamin D test;

Blood tests including Rast test to determine the substances a subject is allergic to, ESR test checks for inflammation where red blood cells aggregate, Vitamin B12 test to measure the amount of vitamin B12 (cobalamin) in the blood, HDL test for level of "good cholesterol" in blood, LDL test for level of "bad cholesterol" in the blood, CRP to test for the level of inflammation with the body, CBC to provide 15 different blood test readings; INR is a blood clotting test, LFT (Liver function test) test for the levels of waste products, enzymes and proteins that are processed by the liver, Urea and Electrolytes test to measure the function of kidney, Comprehensive metabolic panel (CMP) provides the overall picture of the metabolism and chemical balance of the body;

Liver function tests, including but not limit to T-BIL, D-BIL, TP, ALB, GLO, A/G ratio, ALP, AST, ALT, GGT, LDH;

Renal function tests, including but not limit to Urea, CRE, EGFR, Na, K, Cl;

Uric acid tests, including UA;

Hepatitis B tests including but not limit to HBsAg, Anti-HBs;

Tumors Markers tests including but not limit to CEA, CA15-3, CA125, PSA, CA19-9;

Thyroid function tests, including but not limit to TSH, F-T4;

Tissue inflammation screening, including but not limit to CRP, RA factor, pepsinogen, ESR;

Sexually transmitted disease screening, including not limit to syphilis TP-Ab, HIV;

Blood grouping tests, as ABO, Rh(D);

Urinalysis including appearance, PRO, GLU, BIL, URO, RBC, ET, NIT, LEU, SG, pH, Urine sediments;

Fecal occult blood tests including FOBT;

Smear screening including but not limit to Pap Smear;

Allergies and Sensitivities tests including but not limit to IgE test and IgG test;

Biochemical tests, including but not limit to the Kastle-Meyer test tests for the presence of blood in any biofluidic, salicylate testing which is a category of drug, the phadebas test tests for the presence of saliva for forensic purposes, iodine solution tests for starch, the Van Slyke determination tests for specific amino acids, the Zimmermann test for Ketosteroids, Seliwanoff's test for differentiating between aldose and ketose sugars, test for lipids, Sakaguchi test for the presence of arginine in protein, Hopkins Cole reaction for the presence of tryptophan in proteins, Nitroprusside reaction for the presence of free thiol groups of cysteine in proteins, Sullivan reaction for the presence of cysteine and cystine in proteins, Acree-Rosenheim reaction for the presence of tryptophan in proteins, Pauly reaction for presence of tyrosine or histidine in proteins, Heller's test for presence of albumin in urine, Gmelin's test for the presence of bile pigments in urine, Hay's test for the presence of bile pigments in urine and others;

Biochemical tests, including but not limit to Barfoed's test tests for reducing polysaccharides or disaccharides, Benedict's reagent tests for reducing sugars or aldehydes, Fehling's solution tests for reducing sugars or aldehydes, Molisch's test for carbohydrates, Nylander's test for reducing sugars, Rapid furfural test to distinguish between glucose and fructose, the Bicinchoninic acid assay tests for proteins, Biuret reagent tests for proteins and polypeptides, Bradford protein assay measures protein quantitative, The Phadebas Amylase Test determines alpha-amylase activity; Bial's test to test for pentoses, Urea breath test used to identify infections by *Helicobacter pylori*, Wassermann test which is an antibody test for syphilis;

Organic tests, including but not limit to the Carbylamine reaction tests for primary amines, the Griess test tests for organic nitrite compounds, the Iodoform reaction tests for the presence of methyl ketones, or compounds which can be oxidized to methyl ketones, the Schiff test detects aldehydes, tollens' reagent (Silver Mirror) tests for aldehydes, the Zeisel determination tests for the presence of esters or ethers, Lucas' reagent is used to determine mainly between primary, secondary and tertiary alcohols, the Bromine test is used to test for the presence of unsaturation and phenols, radiocarbon dating method to determine the age of an object containing organic material, Baeyer's test to test for Alkaline KMnO4, Liebermann's test for the detection of cholesterol, phthalein dye test to test for phenol;

Inorganic tests, including but not limit to Barium chloride tests for sulfates, the Beilstein test tests for halides qualitatively, Borax bead test tests for certain metals, the Carius halogen method measures halides quantitatively, chemical test for cyanide tests for the presence of cyanide, CN—Copper sulfate tests for presence of water, flame tests test for metals, the Gilman test tests for the presence of a Grignard reagent, the Kjeldahl method quantitatively determines the presence of nitrogen, Nessler's reagent tests for the presence of ammonia, Ninhydrin tests for ammonia or primary amines, Phosphate test for phosphate, the sodium fusion test tests for the presence of nitrogen, sulfur, and halides in a sample, the Zerewitinoff determination tests for any acidic hydrogen, the Oddy test for acid, aldehydes, and sulfides, Gunzberg's test tests for the presence of hydrochloric acid, Kelling's test tests for the presence of lactic acid, Marsh test for the detection of arsenic.

A device of any prior device embodiment, has the function of following tests:
  Composition analysis as identification of fibres, blend analysis and others;
  Color fastness tests in washing, laundering, bleaching and others;
  Wet processing analysis for scouring and bleaching in lab sample and others; Defect analysis of samples;
  General chemical tests including carbonization, dissolution, stripping and redyeing, absorbency of textiles, bleaching loss, dry shrinkage and others;
  Parameter tests including density, nitrogen content, foaming propensity, emulsion stability and others;
  Water, effluent & sludge analysis including pH, density, conductivity, odor, turbidity, total dissolved solids, total hardness, acidity, total chlorine and others;
  Eco parameters tests including free formaldehyde, copper, cobalt, lead, mercury, polyvinyl chloride, APEO/NPEO tests and others;

The biological, chemical, and functional tests in above embodiments, include, for example, immunoassay test, nucleic acid assay test, colorimetric assay test, cell counting test, nucleic acid amplification test, biological image test, chemical image test.

A device of any prior device embodiment, has following function and purposes:
  1) Determine the interactions of a sample with other known substances;
  2) Determine the composition of a sample;
  3) Provide standard data for other scientific, medical, and quality assurance functions;
  4) Validate suitability for end-use;
  5) Provide a basis for technical communication;
  6) Provide a technical means of comparison of several options;
  7) Provide evidence in legal proceedings;
  8) Determine if, or verify that, the requirements of a specification, regulation, or contract are met.

A-4. QMAX Device with Different Level Heights (061)

Figure 2:
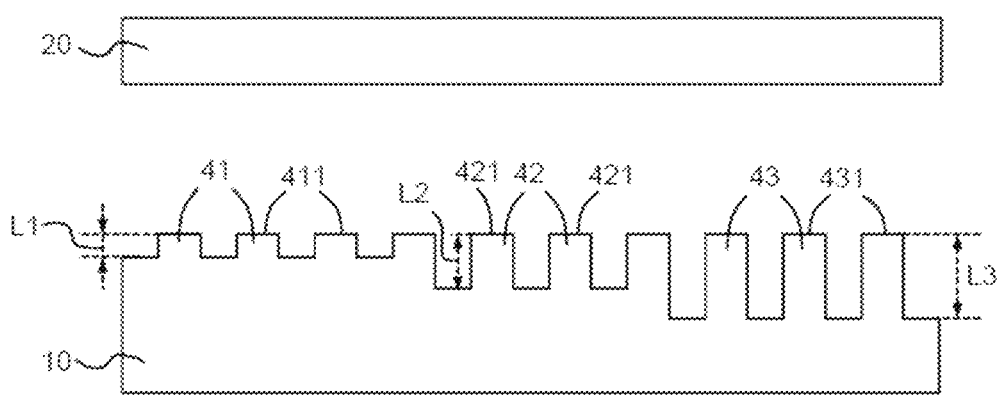
FIG. 2 shows schematics of an exemplary embodiment of a QMAX device, which comprises spacers of different level heights.
Figure 2:
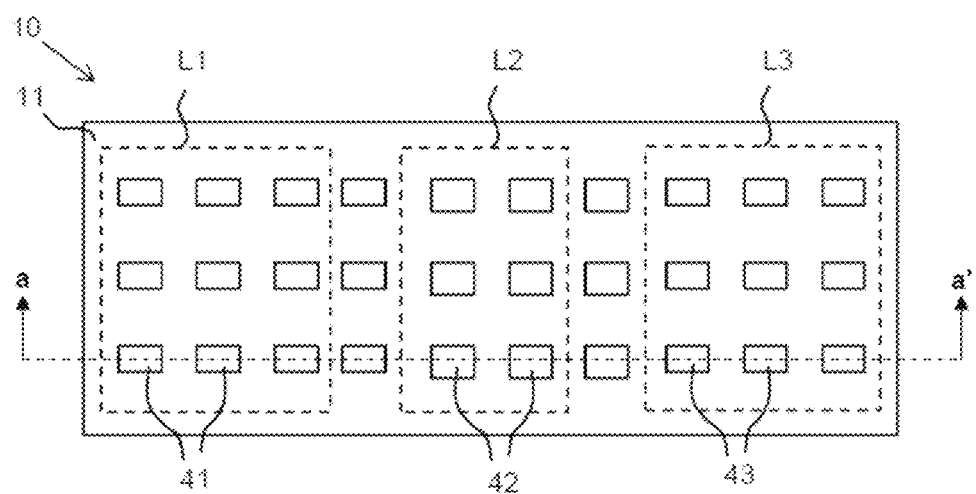

FIG. 2 shows schematics of an exemplary embodiment of a QMAX device, which comprises a first plate 10, a second plate 20, and a plurality of spacers (41, 42, 43) fixed on the inner surface of the first plate 11 (not indicated in cross-sectional view). Panel (A) shows a cross-sectional view of the device, while panel (B) shows a top view of the first plate 10 and the spacers (41, 42, and 43). However, it should be noted that, in some embodiments, the spacers are fixed on the second plate 20, or both the first and second plates. As shown in panel (A), the first plate 10 has different thickness at different locations. Each spacer has a top end and a height that is the vertical distance measured from the top end to the closest point on the inner surface adjacent to the spacer. As shown in the figure, there are three different sets of spacers 41, 42, and 43. Each set of spacers have the same height, i.e. spacers 41 have a height L1, spacers 42 have a height L2, and spacers 42 have a height L3. Different sets of spacers differ from one another at least in their heights, i.e., L1, L2, and L3 are different from one another. On the other hand, the top end of each spacer (411, 421, and 431 as indicated in the cross-sectional view) are substantially aligned on the same plane, as indicated by the dashed line in panel (A). Structurally the spacers in different sets seem to "stem from" different levels of the first plate inner surface. Therefore, the height of the spacers is also termed as "level height" in this context. As such, the QMAX device as shown in FIG. 2 is said to have different level heights. However, it should be noted that, in some embodiments, there are more than one set of spacers having different level heights. In some embodiments, there are 2 sets or more, 3 sets or more, 4 sets or more, 5 sets or more, 6 sets or more, 7 sets or more, 8 sets or more, 9 sets or more, 10 sets or more, 15 sets or more, 20 sets or more, 30 sets or more, 50 sets or more of spacers having different level heights.

Examples of Present Invention

A1. A Device for Analyzing a Liquid Sample, Comprising:
  a first plate, a second plate, and spacers, wherein:
  vi. the plates are movable relative to each other into different configurations;
  vii. one or both plates are flexible, resilient, or both;
  viii. the first plate has, on its inner surface, a first and a second sample contact areas at different locations, and the first plate has a first and second thickness at the first and second sample contact areas, respectively, wherein the sample contact areas are for contacting a sample containing a target analyte or is suspected of containing a target analyte, and wherein the first thickness is different from the second thickness;
  ix. the spacers are fixed to the first plate inner surface, and have a predetermined substantially uniform height in each sample contact area; and
  x. each of the spacers has a top end, and the top ends of the spacers are substantially aligned in one plane or in one surface;
  wherein one of the configurations is an open configuration where the two plates are partially or entirely separated apart, the spacing between the plates is not regulated by the spacers, and the sample is deposited on one or both of the plates; and
  wherein another of the configurations is a closed configuration, which is configured after the sample deposition in the open configuration, and in the closed configuration: at least part of the deposited sample is compressed by the two plates into a layer that is confined by the two plates and has a substantially uniform thickness over each of the respective sample contact areas, and the uniform thickness of the layer is confined by the respective sample contact area and is regulated by the plates and the spacers in the respective sample contact area.

A2. The device of paragraph A1, wherein the uniform heights of the spacers are from 0.5 to 100 μm.

A3. The device of any one of prior paragraphs, wherein the uniform heights of the spacers are from 0.5 to 20 microns.

A4. The device of any one of prior paragraphs, wherein the difference between the uniform heights of the spacers in the first and second sample contact areas is from 0.5 to 100 microns.

A5. The device of any one of prior paragraphs, wherein the difference between the uniform heights of the spacers in the first and second sample contact areas is from 0.5 to 50 microns.

A6. The device of any one of prior paragraphs, wherein the spacers have a predetermined substantially constant inter-spacer distance in each sample contact area.

A7. The device of paragraph A6, wherein the constant inter-spacer distances of the spacers are from 7 to 200 microns.

A8. The device of paragraph A6, wherein the constant inter-spacer distances of the spacers are from 50 to 150 microns.

A9. The device of any one of prior paragraphs, wherein a separation between edges of neighboring sample contact areas is in the range of 20 microns to 1 mm.

A10. The device of any one of prior paragraphs, wherein a separation between edges of neighboring sample contact areas is from 100 to 500 microns.

A11. The device of any one of prior paragraphs, wherein an average value of the uniform thickness of the layer in each sample contact area is substantially the same as the uniform height of the spacers therein with a variation of less than 10%.

A12. The device of any one of prior paragraphs, wherein the first plate has, on at least one of the sample contact areas, a binding site that has a predetermined lateral area and contains a capture agent capable of binding and immobilizing the target analyte.

A13. The device of paragraph A12, wherein in the closed configuration, the uniform thickness of the layer in any one of the sample contact areas is substantially less than the predetermined lateral area of the binding site therein.

A14. The device of any one of prior paragraphs, wherein the second plate has a first and a second sample contact areas at different locations that are corresponding to the first and the second sample contact areas of the first plate, respectively, wherein the respectively corresponding sample contact areas are over one another in the closed configuration.

A15. The device of paragraph A14, wherein the second plate has, on at least one of the sample contact areas, a storage site that has a predetermined lateral area and contains a detection agent, that upon contacting the sample, dissolves and diffuses in the sample.

A16. The device of any one of prior paragraphs, wherein a smallest separation between edges of neighboring sample contact areas is substantially larger than the distance that a target analyte or detection agent can diffuse in a relevant time, wherein the relevant time is:
  i. about equal to or longer than the time that it takes for the target analyte to diffuse across the thickness of the uniform thickness layer at the closed configuration; and
  ii. shorter than the time that it takes for the target analyte to laterally diffuse across the linear dimension of the predetermined area of the binding site.

A17. The device of any one of prior paragraphs, wherein there is no fluidic isolation between neighboring sample contact areas.

C1. A method for analyzing a liquid sample, comprising the steps of:
  (a) obtaining a sample that contains or is suspected of containing a target analyte;
  (b) obtaining a first plate, a second plate, and spacers, wherein:
    i. the plates are movable relative to each other into different configurations;
    ii. one or both plates are flexible, resilient, or both;
    iii. the first plate has, on its inner surface, a first and a second sample contact areas at different locations, and the first plate has a first and second thickness at the first and second sample contact areas, respectively, wherein the sample contact areas are for contacting a sample that contains or is suspected of containing a target analyte, and wherein the first thickness is different from the second thickness;
    iv. the spacers are fixed to the first plate inner surface, and have a predetermined substantially uniform height in each sample contact area; and
    v. each of the spacers has a top end, and the top ends of the spacers are substantially aligned in one plane or one surface;
  (c) depositing the sample on one or both of the plates when the plates are in the open configuration,
    wherein in the open configuration the two plates are partially or entirely separated apart, the spacing between the two plates is not regulated by the spacers, and the sample is deposited on one or both of the plates;
  (d) after (c), bringing the two plates together and pressing the plates into the closed configuration,
    wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and
    wherein the closed configuration is configured after the sample deposition in the open configuration, and in the closed configuration: at least part of the deposited sample is compressed by the two plates into a layer that is confined by the two plates and has a respective substantially uniform thickness over each of the sample contact areas, wherein the uniform thickness of the layer is confined by the respective sample contact area of the plates and is regulated by the plates and the spacers in the respective sample contact area;
  and
  (e) analyzing the target analyte in the layer of uniform thickness when the plates are in the closed configuration.

C2. The method of any one of paragraph C1 or CC1, wherein the uniform heights of the spacers are from 0.5 to 100 μm.

C3. The method of any one of prior method paragraphs, wherein the uniform heights of the spacers are from 0.5 to 20 μm.

C4. The method of any one of prior method paragraphs, wherein the difference between the uniform heights of the spacers in the different sample contact areas is from 0.5 to 100 microns.

C5. The method of any one of prior method paragraphs, wherein the difference between the uniform heights of the spacers in the different sample contact areas is from 0.5 to 50 microns.

C6. The method of any one of prior method paragraphs, wherein the spacers have a predetermined substantially constant inter-spacer distance in each sample contact area.

C7. The method of paragraph C6, wherein the constant inter-spacer distances of the spacers are from 7 to 200 microns.

C8. The method of paragraph C6, wherein the constant inter-spacer distances of the spacers are in the range of from 50 to 150 microns.

C9. The method of any one of prior method paragraphs, wherein a separation between edges of neighboring sample contact areas is in the range of from 20 microns to 1 mm.

C10. The method of any one of prior method paragraphs, wherein a separation between edges of neighboring sample contact areas is in the range of from 100 to 500 microns.

C11. The method of any one of prior method paragraphs, wherein an average value of the uniform thickness of the layer in each sample contact area is substantially the same as the uniform height of the spacers therein with a variation of less than 10%.

C12. The method of any one of prior method paragraphs, further comprising: after step (d) and before step (e), removing the conformable pressing force, wherein the thickness of the layer of uniform thickness after removal of the conformable pressing force: (i) is substantially the same as of the layer of uniform thickness before removing the conformable pressing force; and (ii) deviates from the spacer height by less than 10%.

C13. The method of any one of prior method paragraphs, wherein the conformable pressing is performed by human hand.

C14. The method of any one or prior method paragraphs, wherein the conformable pressing is provided by a pressured liquid, a pressured gas, or a conformable material.

C15. The method of any one of prior method paragraphs, wherein the sample deposition of step (c) is a deposition directly from a subject to the plate without using any transferring devices.

C16. The method of any one of prior method paragraphs, wherein during the deposition of step (c), the amount of the sample deposited on the plate is unknown.

C17. The method of any one or prior method paragraphs, wherein the analyzing in step (e) comprises performing an assay in the layer of uniform thickness.

C18. The method of paragraph C17, wherein the assay is a binding assay or biochemistry assay.

C19. The method of any one of prior method paragraphs, wherein the first plate has, on at least one of the sample contact areas, a binding site that has a predetermined lateral area and contains a capture agent capable of binding and immobilizing the target analyte.

C20. The method of paragraph C19, wherein in the closed configuration, the uniform thickness of the layer in any one of the sample contact areas is substantially less than the predetermined lateral area of the binding site therein.

C21. The method of any one of prior method paragraphs, wherein the second plate has, on at least one of the sample contact areas, a storage site that has a predetermined lateral area and contains a detection agent of a concentration, that upon contacting the sample, dissolves and diffuses in the sample.

C22. The method of any one of prior method paragraphs, wherein a smallest separation between the edges of neighboring sample contact areas is substantially larger than the distance that a target analyte or detection agent can diffuse in a relevant time, wherein there is no fluidic isolation between the neighboring sample contact areas, wherein the relevant time length is:
  i. about equal to or longer than the time that it takes for the target analyte to diffuse across the thickness of the uniform thickness layer at the closed configuration; and
  ii. shorter than the time that it takes the target analyte to laterally diffuse across the linear dimension of the predetermined area of the binding site.

C23. The method of any one of prior method paragraphs, wherein the analyzing of step (e) comprises:
  (1) incubating the sample for a relevant time length and then stopping the incubation; or
  (2) incubating the sample for a time that is equal or longer than the minimum of a relevant time length, and then assessing, within a time period that is equal to or less than the maximum of the relevant length of time, the binding of each target analyte to a binding site,
thereby producing a reaction in which, at the end of the incubation in (1) or during the assessing in (2), the majority of the target analyte in the capture agent-target analyte-detection agent sandwich bound to each binding site is from a corresponding relevant volume of the sample;
  wherein the incubation allows each target analyte to bind to a binding site and a detection agent, wherein the corresponding relevant volume is a portion of the sample that is above the corresponding storage site at the closed configuration.

C24. The method of any one of prior method paragraphs, wherein the reaction is saturated in less than 60 seconds.

C25. The method of any one or prior method paragraphs, wherein the relevant time length is in the range of 60 seconds to 30 minutes.

C26. The method of any one of prior method paragraphs, wherein the analyzing in step (e) comprises measuring a target analyte-related signal selected from the group consisting of:
  i. luminescence selected from photoluminescence, electroluminescence, or electrochemiluminescence;
  ii. light absorption, reflection, transmission, diffraction, scattering, or diffusion;
  iii. surface Raman scattering;
  iv. electrical impedance selected from resistance, capacitance, or inductance;
  v. magnetic relaxivity; and
  vi. any combination of i-v,
  wherein the target analyte-related signal is a signal that is proportional to and reflects the amount of the target analyte in the sample.

C27. The method of paragraph C26, wherein the analyzing step (e) comprises:
  determining an optimal signal from the target analyte-related signals measured from relevant sample contact areas, wherein the relevant sample contact areas are the sample contact areas that contain the binding site, storage site, or both sites, for detecting the same target analyte.

C28. The method of paragraph C26, wherein the optimal target analyte-related signal is determined by selecting the measured target analyte-related signal within a range between minimum and maximum detection thresholds, wherein the minimum and maximum detection thresholds of the plates and a detector are used for the signal measuring.

C29. The method of paragraph C26, wherein the optimal target analyte-related signal is determined by selecting the measured target analyte-related signal within a linear detection range of the assay, wherein the linear detection range is a range of the strength of target analyte-related signal, within which the signal strength has a linear correlation with the amount of the assayed target analyte.

C30. The method of any one of prior method paragraphs, wherein the analyzing step (e) comprises calculating the volume of a relevant sample volume by measuring the lateral area of the relevant sample volume and calculating the volume from the lateral area and the predetermined spacer height, wherein the relevant volume is a part of or an entire volume of the sample.

C31. The method of any one of prior method paragraphs, wherein the analyzing step (e) comprises reading the target analyte, image analysis of the target analyte, counting of the target analyte, or a combination of thereof.

C32. The method of any one of prior method paragraphs, further comprising one or more washes. Example of the wash steps wash the plates (first plate or second plate) to (1) remove the unbinding analyte, (2) remove the unbinding detection analyte, (3) remove the non-specific analyte using washing solvent as PBST.

C33. The method of any one of prior method paragraphs, wherein the deposited sample has a total volume less 0.5 microliters.

C34. The method of any one of prior method paragraphs, wherein the liquid sample is made from a biological sample selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

C35. The method of any one of prior method paragraphs, wherein the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

C36. The method of any one of prior method paragraphs, wherein the sample is an environmental gaseous sample from a source selected from the group consisting of: the air, underwater heat vents, industrial exhaust, vehicular exhaust, and any combination thereof.

C37. The method of any one of prior method paragraphs, wherein the sample is a foodstuff sample selected from the group consisting of: raw ingredients, cooked food, plant and animal sources of food, preprocessed food, and partially or fully processed food, and any combination thereof.

C38. The method of any one of prior method paragraphs, wherein the sample is human blood, and the depositing step comprises: (a) pricking the skin of a human to release a droplet of blood onto the skin; and (b) contacting the droplet of blood with one of the plate of the device without use of a blood transfer tool.

D1. A method for a parallel multiplexed assay of a liquid sample, comprising the steps of:
  (a) obtaining a sample suspected of containing a target analyte
  (b) obtaining a first plate, a second plate, and spacers, wherein:
    i. the plates are movable relative to each other into different configurations, including an open configuration and a closed configuration;
    ii. one or both of the plates are flexible;
    iii. the first plate has, on its inner surface, a first and a second sample contact areas at different locations, and the first plate has a first and second thickness at the first and second sample contact areas, respectively, wherein the sample contact areas are for contacting a sample containing or suspected of containing a target analyte, and wherein the first thickness is different from the second thickness;
    iv. the first plate has, on at least one of the sample contact areas, a binding site that has a predetermined lateral area and contains a capture agent capable of binding and immobilizing the target analyte;
    v. the second plate has, on at least one of the sample contact areas, a storage site that has a predetermined lateral area and contains a detection agent, that upon contacting the sample, dissolves and diffuses in the sample;
    vi. the spacers are fixed to the respective inner surface of one or both of the plates and have a predetermined substantially uniform height in each sample contact area; and
    vii. each of the spacers has a top end, and the top ends of the spacers are substantially aligned in one surface;
  wherein each capture agent, target analyte and corresponding detection agent are capable of forming a capture agent-target analyte-detection agent sandwich in a binding site of the first plate;
  (c) depositing the sample on one or both of the plates when the plates are in the open configuration,
    wherein the open configuration is a configuration in which the two plates are partially or entirely separated apart, the spacing between the plates is not regulated by the spacers, and the sample is deposited on one or both of the plates;
  (d) after (c), bringing the two plates together and pressing the plates into the closed configuration,
    wherein the pressing comprises conformable pressing, either in parallel or sequentially, an area of at least one of the plates to press the plates together to the closed configuration, wherein the conformable pressing generates a substantially uniform pressure on the plates over the at least part of the sample, and the pressing spreads the at least part of the sample laterally between the inner surfaces of the plates; and
    wherein the closed configuration is configured after the sample deposition at the open configuration, and in the closed configuration: the corresponding sample contact areas on the two plates are over one another, respectively; and at least part of the deposited sample is compressed by the two plates into a layer that is confined by the two plates and has a respective substantial uniform thickness over each of the sample contact areas, wherein the uniform thickness of the layer is confined by the respective sample contact area of the plates and is regulated by the plates and the spacers in the respective sample contact area; and
  (e) after (d) and while the plates are in the closed configuration:

(1) incubating the sample for a relevant time length and then stopping the incubation; or (2) incubating the sample for a time that is equal or longer than the minimum of a relevant time length, and then assessing, within a time period that is equal to or less than the maximum of the relevant length of time, the binding of each target analyte to a binding site, thereby producing a reaction in which, at the end of the incubation in (1) or during the assessing in (2), the majority of the target analyte in the capture agent-target analyte-detection agent sandwich bound to each binding site is from a corresponding relevant volume of the sample;

wherein the incubation allows each target analyte to bind to a binding site and a detection agent, wherein the corresponding relevant volume is a portion of the sample that is above the corresponding storage site at the closed configuration, and wherein the relevant time is:

(i) about equal to or longer than the time that it takes for the target analyte to diffuse across the thickness of the uniform thickness layer at the closed configuration; and (ii) shorter than the time that it takes for the target analyte to laterally diffuse across the linear dimension of the predetermined area of the binding site.

D3. The method of paragraph D2, wherein the analyzing step (e) comprises:

determining an optimal signal from the target analyte-related signals measured from relevant sample contact areas, wherein the relevant sample contact areas are the sample contact areas that contain the binding site, storage site, or both sites, for detecting the same target analyte.

D4. The method of paragraph D3, wherein the optimal target analyte-related signal is determined by selecting the measured target analyte-related signal within a range between minimum and maximum detection thresholds, wherein the minimum and maximum detection thresholds of the plates and a detector are used for the signal measuring.

D5. The method of paragraph D3, wherein the optimal target analyte-related signal is determined by selecting the measured target analyte-related signal within a linear detection range of the assay, wherein the linear detection range is a range of the strength of target analyte-related signal, within which the signal strength has a linear correlation with the amount of the assayed target analyte.

E1. The device or method of any one of prior paragraphs, wherein the binding site is defined by a patch of dried reagent.

E2. The device or method of any one of prior paragraphs, wherein the binding site is between a pair of electrodes.

E3. The device or method of any one of prior paragraphs, wherein one or both plate inner surfaces comprise one or a plurality of amplification sites that are each capable of amplifying the target analyte-related signal when the target analyte is within 500 nm from an amplification site.

E4. The device or method of any one of prior paragraphs, wherein the plates have a thickness of less than 200 μm.

E5. The device or method of any one of prior paragraphs, wherein the plates have a thickness of less than 100 μm.

E6. The device or method of any one of prior paragraphs, wherein each of the plates has an area of less than 5 cm$^2$.

E7. The device or method of any one of prior paragraphs, wherein each of the plates has an area of less than 2 cm$^2$.

E8. The device or method of any one of prior paragraphs, wherein at least one of the plates is partially or entirely transparent.

E9. The device or method of any one of prior paragraphs, wherein at least one of the plates is made from a flexible polymer.

E10. The device or method of any one of prior paragraphs, wherein at least one of the plates is a flexible plate, and the thickness of the flexible plate times the Young's modulus of the flexible plate is in the range of 60 to 75 GPa-μm.

E11. The device or method of any one of prior paragraphs, wherein the spacers are spacers with a cross sectional shape selected from round, polygonal, circular, square, rectangular, oval, elliptical, or any combination of the same.

E12. The device or method of any one of prior paragraphs, wherein the spacers have a pillar shape and a substantially flat top surface, wherein, for each spacer, the ratio of the lateral dimension of the spacer to its height is at least 1.

E13. The device or method of any one of prior paragraphs, wherein each spacer has the ratio of the lateral dimension of the spacer to its height is at least 1.

E14. The device or method of any one of prior paragraphs, wherein the minimum lateral dimension of spacer is less than or substantially equal to the minimum dimension of a target analyte in the sample.

E15. The device or method of any one of prior paragraphs, wherein the spacers have a pillar shape, and the sidewall corners of the spacers have a round shape with a radius of curvature at least 1 μm.

E16. The device or method of any one of prior paragraphs, wherein the spacers have a density of at least 100/mm$^2$.

E17. The device or method of any one of prior paragraphs, wherein the spacers have a density of at least 1000/mm$^2$.

E18. The device or method of any one of prior paragraphs, wherein the spacers have a filling factor of at least 1%, wherein the filling factor is the ratio of the spacer area in contact with the layer of uniform thickness to the total plate area in contact with the layer of uniform thickness.

E19. The device or method of any one of prior paragraphs, wherein the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

E20. The device or method of any one of prior paragraphs, wherein a. at least one of the plates is flexible, resilient, or both, and b. for the flexible plate, the fourth power of the inter-spacer-distance (ISD) divided by the thickness of the flexible plate (h) and the Young's modulus (E) of the flexible plate, $ISD^4/(hE)$, is equal to or less than 106 um$^3$/GPa.

E21. The device or method of any one of prior paragraphs, wherein the spacers are fixed on a plate by directly embossing the plate or injection molding of the plate.

E22. The device or method of any one of prior paragraphs, wherein the materials of the plate and the spacers are independently selected from polystyrene, PMMG, PC, COC, COP, or another plastic.

M2 An embodiment of a method for fabricating the Q-Card of any embodiments of MA1 to MA4, comprising:

(a) Laser cutting the first plate, (b) nanoimprinting or extrusion printing of the second plate.

M3 An embodiment of a method for fabricating the Q-Card of any embodiments of MA1 to MA4, comprising:

(a) Injection molding and laser cutting the first plate, (b) nanoimprinting or extrusion printing of the second plate.

M4 An embodiment of a method for fabricating the Q-Card of any embodiments of MA1 to MA4, comprising: nanoimprinting or extrusion printing to fabricated both the first and the second plate.

M5 An embodiment of a method for fabricating the Q-Card of any embodiments of MA1 to MA4, comprising: fabricating the first plate or the second plate, using injection molding, laser cutting the first plate, nanoimprinting, extrusion printing, or a combination of thereof.

The method of any embodiments of M1-M5, wherein the method further comprises a step of attach the hinge on the first and the second plates after the fabrication of the first and second plates.

B. QMAX Device with Different Spacer Heights

B-1. Examples of QMAX Device with Different Spacer Heights

One aspect of the present invention provides a QMAX device for analyzing a liquid sample, which comprises spacers of different heights.

Figure 3:
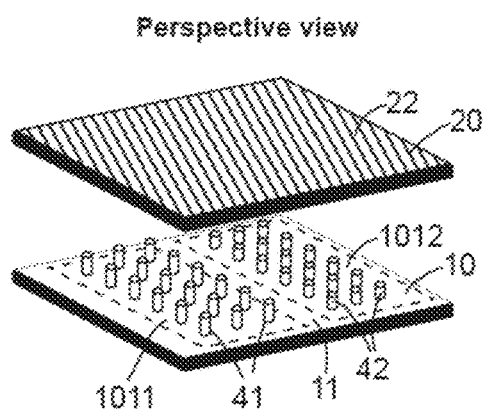
FIG. 3 illustrates an embodiment of a QMAX device that comprises two sets of spacers, each of which has a uniform height that is different from that of the other set. Panel (A) shows a prospective view of a first plate, a second plate and spacers; panel (B) shows prospective and sectional views of depositing a sample on one of the plates; panel (C) shows using the first plate and the second plate to compress the sample into a layer of uniform thickness, which is regulated by the height of the spacers.
Figure 3:
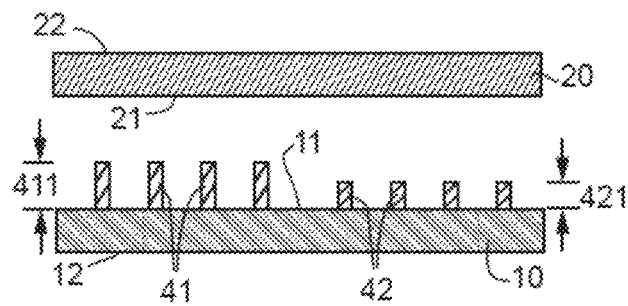
Figure 3:
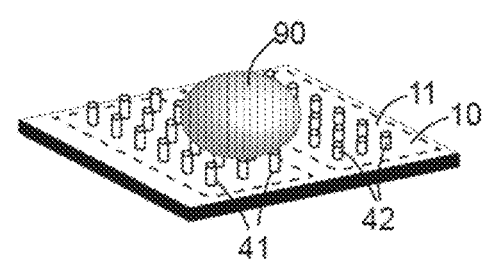
Figure 3:
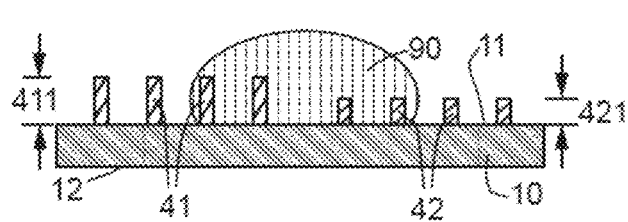
Figure 3:
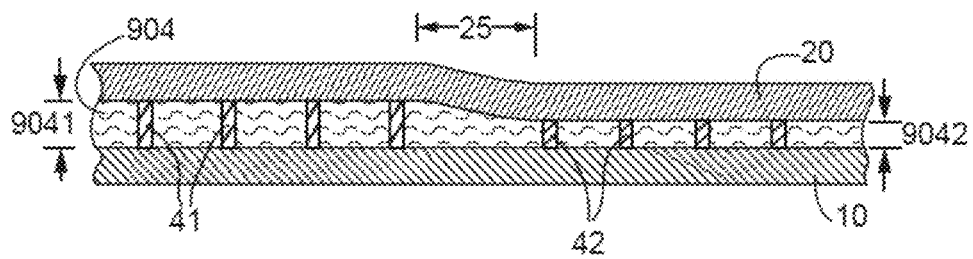

FIG. 3 schematically shows one embodiment of the QMAX device, which comprises a first plate 10 and a second plate 20. In particular, panel (A) shows both the perspective and cross-sectional views of the first plate 10 and the second plate 20. Each of the plates respectively comprises an inner surface (11 and 21) and an outer surface (12 and 22). The first plate 10 has, on its inner surface 11, a first sample contact area 1011 at one location and a second sample contact area 1012 at another location. The second plate 20 also has, on its inner surface 21, a first and a second sample contact area (not shown) that are corresponding to the first sample contact area 1011 and the second sample contact area 1012 of the first plate, respectively. (The meaning of "corresponding" is discussed in details below). The sample contact areas are for contacting a sample to be analyzed using the device. Further, as illustrated, the first plate 10 comprises a plurality of spacers (41 and 42). It should be noted, however, in some embodiments, the second plate 20 or both the first plate 10 and second plate 20 have the spacers on the respective inner surfaces. In some embodiments, the spacers (42 and 42) are fixed to one or both of the plates 10 and 20. Herein the term "fixed" means that the spacers are attached to a plate and the attachment is maintained during one or more uses of the plate.

In some embodiments, the QMAX device in the present invention include but not be limited to the QMAX device described in U.S. Provisional patent Application No. 62/202,989, which was filed on Aug. 10, 2015, U.S. Provisional patent Application No. 62/218,455, which was filed on Sep. 14, 2015, U.S. Provisional patent Application No. 62/293,188, which was filed on Feb. 9, 2016, U.S. Provisional patent Application No. 62/305,123, which was filed on Mar. 8, 2016, U.S. Provisional patent Application No. 62/369,181, which was filed on Jul. 31, 2016, U.S. Provisional patent Application No. 62/394,753, which was filed on Sep. 15, 2016, PCT Application (designating U.S.) No. PCT/US2016/045437, which was filed on Aug. 10, 2016, PCT Application (designating U.S.) No. PCT/US2016/051775, which was filed on Sep. 14, 2016, PCT Application (designating U.S.) No. PCT/US2016/051794, which was filed on Sep. 15, 2016, and PCT Application (designating U.S.) No. PCT/US2016/054025, which was filed on Sep. 27, 2016, the complete disclosures of which are hereby incorporated by reference for all purposes.

In some embodiments, there are at least one of the spacers inside the first sample contact area 1011 and the second sample contact area 1012, respectively. As illustrated in FIG. 3, the spacers 41 and 42 are inside the first sample contact area 1011 and the second sample contact area 1012, respectively. The spacers over the first sample contact area 41 (hereinafter "the first set of spacers") have a first uniform height 411 and a uniform inter-spacer distance, and so do the spacers over the second sample contact area 42 (hereinafter "the second set of spacers"). In some embodiments, the first uniform height 411 is different from the second uniform height 421 of the second set of spacers 42. In some embodiments, the first or the second uniform height is 10 nm or more, 20 nm or more, 50 nm or more, 100 nm or more, 200 nm or more, 500 nm or more, 1 um or more, 2 um or more, 5 um or more, 10 um or more, 20 um or more, 50 um or more, 100 um or more, 200 um or more, 500 um or more, 1 mm or more, 750 um or less, 250 um or less, 150 um or less, 75 um or less, 25 um or less, 15 um or less, 7.5 um or less, 1.5 um or less, 750 nm or less, 250 nm or less, 150 nm or less, 75 nm or less, 25 nm or less, or 15 nm or less. In some embodiments, the difference between the first and second uniform heights is 5 nm or more, 10 nm or more, 20 nm or more, 50 nm or more, 100 nm or more, 200 nm or more, 500 nm or more, 1 um or more, 2 um or more, 5 um or more, 10 um or more, 20 um or more, 50 um or more, 100 um or more, 200 um or more, 500 um or more, 1 mm or more, 750 um or less, 250 um or less, 150 um or less, 75 um or less, 25 um or less, 15 um or less, 7.5 um or less, 1.5 um or less, 750 nm or less, 250 nm or less, 150 nm or less, 75 nm or less, 25 nm or less, 15 nm or less, or 7.5 nm or less.

In some embodiments, the spacers have a constant inter-spacer distance. In some embodiments, the first set spacers have a first constant inter-spacer distance, the second set spacers have a different second constant inter-spacer distance. In some embodiments, the constant inter-spacer distance is 10 nm or more, 20 nm or more, 50 nm or more, 100 nm or more, 200 nm or more, 500 nm or more, 1 um or more, 2 um or more, 5 um or more, 10 um or more, 20 um or more, 50 um or more, 100 um or more, 200 um or more, 500 um or more, 1 mm or more, 750 um or less, 250 um or less, 150 um or less, 75 um or less, 25 um or less, 15 um or less, 7.5 um or less, 1.5 um or less, 750 nm or less, 250 nm or less, 150 nm or less, 75 nm or less, 25 nm or less, or 15 nm or less. In some embodiments, the constant inter-spacer distance is at least 2 times larger than the size of the target analyte. In some embodiments, the constant inter-spacer distance is up to 200 um.

FIG. 3 further illustrates that the first plate 10 and the second plate 20 are movable relative to each other into different configurations, including an open configuration and a closed configuration. FIG. 3 panels (A) and (B) depict some embodiments of the open configuration. In the open configuration, the two plates are partially or entirely separated apart, and the spacing between the plates is not regulated by the spacers (41 and 42). As shown in panel (B), the spacing between the plates in the open configuration allows the sample 90 to be deposited on the first plate 10. It is to be noted, however, in some embodiments, the sample 90 is deposited either on the second plate 20 or on both plates 10 and 20.

FIG. 3 panel (C) shows the exemplary embodiment of the closed configuration of the two plates, that is configured after the sample deposition as exemplified in FIG. 3 panel (B). In the closed configuration, the two plates are brought to face each other with their inner surfaces 11 and 21. Consequently, at least part of the deposited sample 90 is compressed by the two plates into a layer 904. The layer 904, as shown in the figure, has a first uniform thickness 9041 at the first sample contact area 1011 (not indicated) and a second uniform thickness 9042 at the second sample contact area 1012 (not indicated). In some embodiments, the first and second uniform thickness 9041 and 9042 are regulated by the first and second sets of the spacers 41 and 42, respectively. In some embodiments, the first uniform thickness 9041 is different from the second uniform thickness 9042. It is to be noted that the term "layer of uniform thickness" as used herein refers to a layer of sample that has a uniform thickness across a continuous substantial lateral area thereof, and the uniform thickness is different in one substantial lateral area from another. In some embodiments, the percentage of the whole lateral area of the layer that the substantial lateral area takes up is equal to or more than 10%, 20%, 30%, 40%, 50%, 60%, 70%, 80%, 90%, 95%, 99%, 100%, or a range between any two of the values.

In some embodiments, the respectively corresponding sample contact areas are over one another in the closed configuration, meaning that the first sample contact area on the first plate and its corresponding first sample contact area on the second plate are configured to face each other in the closed configuration and so do the corresponding second sample contact areas on the first and the second plates. The term "corresponding" as used herein in certain contexts of the QMAX device, refers to the relationship between a pair of the subjects (e.g. first or second sample contact area, the binding site, storage site) belonging to each of the two plates of the QMAX device, respectively, that face each other in the closed configuration.

Figure 4:
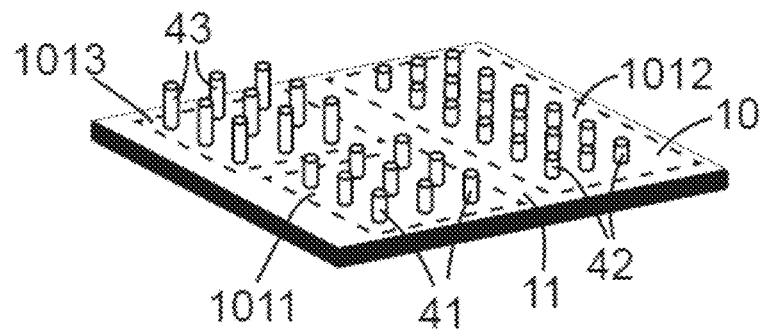
FIG. 4 shows two exemplary embodiments of a QMAX device for analyzing a liquid sample provided by the present invention. Panel (A) shows a device comprising three sets of spacers, each of which has a uniform height that is different from that of other sets, panel (B) shows a device comprising four sets of spacers, each of which has a uniform height that is different from that of other sets.
Figure 4:
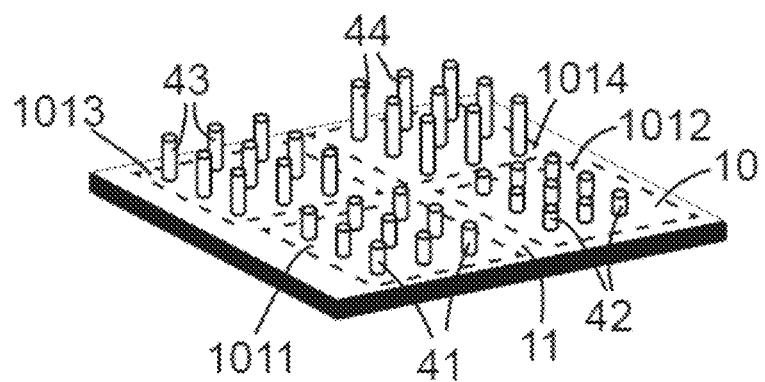

FIG. 4 shows some exemplary embodiments of the device provided by the present invention. As shown in the figure, the device comprises more than two sample contact areas on the first plate 10. Panel (A) shows that the first plate 10 has a first sample contact area 1011, a second contact area 1012, and a third sample contact area 1013. In each sample contact area, there is at least one spacer respectively. Here, spacers 41, 42, and 42 are in the sample contact areas 1011, 1012, and 1013, respectively. In some embodiments, all the three sets of spacers have a respective uniform height that is different from one another. Panel (B) shows another exemplary device, wherein there are four sample contact areas (1011, 1012, 1013, and 1014) and four sets of spacers of different uniform heights (41, 42, 43, and 44). In other embodiments, it is also possible that the number of sample contact areas the device comprises is equal to or more than 5, 6, 7, 8, 9, 10, 20, 30, 50, 75, 100, 200, 500, 1000, or in a range between any two of the values.

In some embodiments, one or both of the first plate 10 and second plate 20 are flexible, in order to enable the formation of the layer of uniform thickness 904 that has different uniform thicknesses at different sample contact areas.

In some embodiments, the distance between two neighboring spacer sets is 10 nm or more, 20 nm or more, 50 nm or more, 100 nm or more, 200 nm or more, 500 nm or more, 1 um or more, 2 um or more, 5 um or more, 10 um or more, 20 um or more, 50 um or more, 100 um or more, 200 um or more, 500 um or more, 1 mm or more, 750 um or less, 250 um or less, 150 um or less, 75 um or less, 25 um or less, 15 um or less, 7.5 um or less, 1.5 um or less, 750 nm or less, 250 nm or less, 150 nm or less, 75 nm or less, 25 nm or less, or 15 nm or less. The term "spacer set" as used herein refers to a group of consecutive spacers having a uniform height, wherein the uniform height is different from that of other spacers on the same QMAX device, for instance, as described above, the first spacer set or the first set of spacers 41 have a first uniform height 411 that is different from the second uniform height 421 of the second spacer set 42. The term "the distance between two neighboring spacer sets" is defined as the minimum distance between two spacers from each of the two neighboring spacer sets. In some embodiments, the distance between two neighboring spacer sets and the flexibility of the two plates are designed in a way that in the closed configuration, part of the sample can be compressed into a layer of uniform thickness that has different and uniform thicknesses at different sample contact areas. In some embodiments, distance between two neighboring spacer sets and the flexibility of the two plates are designed in a way that at any given location of the two plates, the spacing between the two plates is only regulated by the local spacers, but not affected by remote spacers. Consequently, the uniform thickness of the layer across the lateral dimension of the plate is all regulated by the spacers.

In some embodiments, it would be possible to conformable press, either in parallel or sequentially, the QMAX device into a closed configuration. Conformable pressing is a method that makes the pressure applied over an area to be substantially constant regardless of the shape variation of the outer surfaces of the plates; In particular, parallel conformable pressing applies the pressures on the intended area at the same time, and sequential conformable pressing applies the pressure on a part of the intended area and gradually move to other area. Conformable pressing can be applied by human hand, air blow, liquid pressure, or other forces.

In some embodiments, the QMAX device is self-held in the closed configuration after removing the external force that brings the device from an open configuration to the closed configuration. The "self-holding" may be due to the forces existing between the inner surfaces of the two plates than the external force, such as, but not limited to capillary force. In some embodiments, the thickness of the layer of uniform thickness after removal of the external force is substantially the same as of the layer of uniform thickness before removing the conformable pressing force. In some embodiments, after removal of the external force, the thickness of the layer of uniform thickness deviates from the spacer height by a number equal to or less than 50%, 40%, 30%, 20%, 10%, 8%, 5%, 2.5%, 1%, 0.75%, 0.5%, 0.25%, 0.1%, or 0. In some embodiments, after removal of the conformable pressing force, the thickness of the layer of uniform thickness deviates from the spacer height by less than 10%.

B-2. Volume Multiplexing

In some embodiments, the spacers having different heights are capable of adding a layer of multiplexing possibility to the sample analysis the QMAX device may be used for. This is due to the fact that in the layer of uniform thickness, the spacer height regulates the relevant volume of the sample to be analyzed, and therefore the amount of target analytes contained within the relevant volume. The term "relevant volume" refers to a part of or an entire volume of the sample. In some embodiments, in the layer of uniform thickness, the relevant volume of the sample can be determined by measuring the lateral area of the relevant sample volume and calculating the volume from the lateral area and the predetermined spacer height. Therefore, the relevant volume is proportional to the spacer height within a given lateral area of layer of uniform thickness. Consequentially, the amount of target analyte within each sample contact area is proportional to the spacer height. In some embodiments, the different spacer heights render the sample contact areas in contact with different amount of target analyte ("volume multiplexing").

In some embodiments, the QMAX device is used for an assay to analyze a liquid sample, and the sample contact area comprises a binding site and/or a storage site for the assay. The term "binding site" refers to a location on a solid surface that can immobilize an entity in a sample, and the term "storage site" refers to a site of an area on a plate, wherein the site contains reagents to be added into a sample, and the reagents are capable of being dissolving into the sample that is in contact with the reagents and diffusing in the sample.

For multiplexing purposes, in some embodiments, the first plate has, one or a plurality of the sample contact areas, a binding site that has a predetermined area and contains a capture agent capable of binding and immobilizing the target analyte. In some embodiments, the second plate has, one or a plurality of the sample contact areas, a storage site that has a predetermined area and contains a detection agent of a concentration, that upon contacting the sample, dissolves into the sample and diffuses in the sample.

In some embodiments, the plurality of binding sites comprise capture agent of different species or same capture agent of different concentrations. In some embodiments, the plurality of storage sites comprise different detection agents of different species or same detection reagents of different concentrations. In some embodiments, in the closed configuration, the corresponding storage sites are over the binding sites respectively.

In some embodiments of the QMAX device, there is no fluidic isolation between the binding sites and/or the storage sites. In some embodiments, separation between edges of neighboring binding sites and/or neighboring storage sites is larger than the distance that a target analyte or detection agent can diffuse in a relevant time. The term "relevant time" as used herein refers to a time length that is: (i) about equal to or longer than the time that it takes for the target analyte to diffuse across the thickness of the uniform thickness layer at the closed configuration; and (ii) shorter than the time that it takes the target analyte to laterally diffuse across the linear dimension of the predetermined area of the binding site.

In some embodiments, the spacers having different heights are capable of adding another layer of multiplexing possibility to assay, as described above, using the QMAX device. That is on top of having a plurality of binding sites and/or storage sites that comprises different assay reagents (e.g., capture agents, detection agents) or same assay reagents with different concentrations, the QMAX device is capable of offering different sample volumes or different amounts of analyte for multiplexing purposes.

In some embodiments of the QMAX device with volume multiplexing, there is no fluidic isolation between neighboring sample contact areas, and separation between edges of neighboring sample contact areas is larger than the distance that a target analyte or detection agent can diffuse in a relevant time. Therefore, in these embodiments, each sample contact area comprises a unique combination of the spacer height, the binding site, and the storage site. A combination of three different parameters can be tested for an assay in parallel using the same QMAX device.

In some embodiments of the methods using the QMAX device, in order to realize the parallel multiplexed assay, the analyzing step (e) comprises:
 (1) incubating the sample for a relevant time length and then stopping the incubation; or
 (2) incubating the sample for a time that is equal or longer than the minimum of a relevant time length, and then assessing, within a time period that is equal to or less than the maximum of the relevant length of time, the binding of each target analyte to a binding site,
thereby producing a reaction in which, at the end of the incubation in (1) or during the assessing in (2), the majority of the target analyte in the capture agent-target analyte-detection agent sandwich bound to each binding site is from a corresponding relevant volume of the sample;
 wherein the incubation allows each target analyte to bind to a binding site and a detection agent, wherein the corresponding relevant volume is a portion of the sample that is above the corresponding storage site at the closed configuration.

B-3 Assay Optimization and Quantification

In some embodiments, the volume multiplexing rendered by the different spacer heights is useful for assay optimization and obtaining an optimal analyte-related signal in a regular assay. In many cases, bio/chemical assays rely on detecting an analyte by specific reacting with, binding and/or labeling of the analyte with the addition of external assay reagents into the sample. Therefore, one major obstacle in optimizing these assays is to determine the appropriate amount of assay agents added to the sample, in order to obtain an optimal detectable signal that accurately reflects the genuine amount of the analyte in the sample. This usually requires, among many others, a number of factors to be considered:

1) the general amount of assay reagents relative to the potential amount of analyte in the sample. Generally speaking, relatively smaller amount of assay reagents would lead to the risk of undetectable signal, saturation by the analyte, etc.; on the other hand, largely excessive amount of assay reagents is often costly and unnecessary.

2) the relative amount of each assay reagent, such as, but not limited to, binding agent, detection agent, capture agent, primary antibody, secondary antibody, oligonucleotide probe, or staining dye. For instance, in the case of competitive immunoassay, the relative ratio of the two reciprocal binding agents, one of which binds to the analyte and competitively inhibits the binding between the two reciprocal binding agents, is critical for the assay. And often the relative amount of the analyte in the sample determines the optimal ratio of the two reciprocal binding agents, as recognized in the art. Inappropriate amount of either one of the two would lead to false or inaccurate results in regards to the amount of analyte.

3) the detection threshold of the detector as used for receiving and analyzing the analyte-related signal. Detectors usually have a minimum and a maximum detection threshold, defining the lower and upper limit of the strength of the signal, within the range of which the detector is capable of receiving and analyzing the analyte-related signal and giving out meaningful results in regards to the amount of the analyte in the sample.

Given the foregoing factors and many others, conventionally in the art, tedious experimentation for assay optimization that consumes many material resources is required for the development of a valid and optimal bio/chemical assay, and very often such an optimization step is hard to be implemented at the point of use with limited resources and time. In some embodiments of the present invention, the addition of the volume multiplexing by the use of different spacer heights in the QMAX device expands the possibility of testing different combinations of the assay reagents and the sample. In addition to having different amounts or species of assay reagents in different sample contact areas, one can use spacers of different heights to render different sample contact areas in contact with possibly different pre-determined volumes of the sample, and the target analyte-related signals generated therein would consequentially be different and proportional to the spacer heights therein.

In some embodiments, the addition of volume multiplexing renders it possible to obtain an optimal target analyte-related signal from a number of different target analyte-related signals obtained from different sample contact areas, for the analysis of the target analyte in the sample. In some embodiments, the optimal target analyte-related signal is the signal within the minimum and maximum detection thresholds of the detector. In some embodiments, the optimal target analyte-related signal is the signal that accurately reflects the amount of target analyte in the sample, for instance, within the linear detection range of the assay, as understood by skilled artisans in the field.

In some embodiments, the addition of volume multiplexing renders it possible to optimize the assay at the point of use. In some embodiments, the addition of volume multiplexing saves the assay reagents that are needed for optimization, due to the small volume of sample need for the use of QMAX device.

In some embodiments, the reaction is saturated in less than 60 seconds. In some embodiments, the relevant time length is in the range of 60 seconds to 30 minutes.

In some embodiments, the optimal target analyte-related signal is determined by selecting the measured target analyte-related signal within a range between minimum and maximum detection thresholds, wherein the minimum and maximum detection thresholds of the plates and a detector used for the signal measuring.

In some embodiments, the optimal target analyte-related signal is determined by selecting the measured target analyte-related signal within a linear detection range of the assay, wherein the linear detection range is a range of the strength of target analyte-related signal, within which the signal strength has a linear correlation with the amount of the assayed target analyte.

In some embodiments, the analyzing step (e) comprises calculating the volume of a relevant sample volume by measuring the lateral area of the relevant sample volume and calculating the volume from the lateral area and the predetermined spacer height, wherein the relevant volume is a part of or an entire volume of the sample.

In some embodiments, the analyzing step (e) comprises reading, image analysis, or counting of the target analyte, or a combination of thereof.

In some embodiments, the liquid sample is made from a biological sample selected from the group consisting of: amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, urine, and any combination thereof.

In some embodiments, the sample is an environmental liquid sample from a source selected from the group consisting of: river, lake, pond, ocean, glaciers, icebergs, rain, snow, sewage, reservoirs, tap water, or drinking water, solid samples from soil, compost, sand, rocks, concrete, wood, brick, sewage, and any combination thereof.

In some embodiments, the sample is an environmental gaseous sample from a source selected from the group consisting of: the air, underwater heat vents, industrial exhaust, vehicular exhaust, and any combination thereof.

In some embodiments, the sample is a foodstuff sample selected from the group consisting of: raw ingredients, cooked food, plant and animal sources of food, preprocessed food, and partially or fully processed food, and any combination thereof.

the sample is human blood, and the depositing step comprises: (a) pricking the skin of a human release a droplet of blood onto the skin; and (b) contacting the droplet of blood with the filter without use of a blood transfer tool.

Other Examples

1. A device for receiving a liquid sample to be analyzed, the device comprising:
  a first portion configured to receive the liquid sample, the first portion including a top surface, a receiving surface defining a first region and a second region, a first plurality of projections extending transversely from the first region of the receiving surface, and a second plurality of projections extending transversely from the second region of the receiving surface, wherein each of the first plurality of projections includes a first projection top surface and defines a first height, and each of the second plurality of projections includes a second projection top surface and defines a second height, the second height being different from the first height, and the first projection top surfaces and the second projection top surfaces lie in a common plane and together define the top surface of the first portion; and
  a second portion configured to contact the first portion, the second portion including a bottom surface configured to contact the top surface of the first portion.

2. A method of using the device of embodiment 1 to analyze the liquid sample, comprising depositing the liquid sample onto the first region of the receiving surface and onto the second region of the receiving surface, placing the bottom surface of the second portion onto the top surface of the first portion, and coupling the first and second portions with the liquid sample to a mobile device for analysis.

3. A device for receiving a liquid sample to be analyzed, the device comprising:
  a first portion configured to receive the liquid sample, the first portion including a planar bottom surface, a top surface, and a receiving surface, the receiving surface defining a first area having a first plurality of spacers projecting from the receiving surface and defining a first height, and a second area having a second plurality of spacers projecting from the receiving surface and defining a second height, the second height being different from the first height; and
  a second portion configured to contact the first portion, the second portion including a bottom surface configured to contact the top surface of the second portion;
  wherein when the second portion is in contact with the first portion, the device defines a first volume and a second volume, the first volume being defined by the first area of the receiving surface, a portion of the bottom surface of the second portion that is directly opposite the first area and defining a same length and same width as compared to the first area, and the first height of the first plurality of spacers, and the second volume being defined by the second area of the receiving surface, another portion of the bottom surface of the second portion that is directly opposite the second area and defining a same length and same width as compared to the second area, and the second height, and the first volume is different from the second volume.

4. A method of using the device of any prior embodiment to analyze the liquid sample, comprising depositing the liquid sample onto the first area of the receiving surface and onto the second area of the sample-receiving surface, placing the bottom surface of the second portion onto the top surface of the first portion, and coupling the first and second portions with the liquid sample to a mobile device for analysis.

5. A system for receiving and preparing a liquid sample for analysis by a mobile device, the system comprising:
   a sample-receiving device with multiple, distinct regions, including a first area and a second area, for receiving the liquid sample, the device including:
   a first device portion configured to receive the liquid sample, the first device portion including a top surface, a bottom surface, and a receiving surface between the top surface and the bottom surface, the receiving surface defining the first area having a first plurality of spacers projecting from the receiving surface, and defining the second area having a second plurality of spacers projecting from the receiving surface, the first spacers defining a first height, the second spacers defining a second height, the second height being greater than the first height; and
   a second portion configured to contact the first portion, the second portion including a top surface and a bottom surface, the bottom surface of the second portion configured to contact the top surface of the first portion;
   an interface device configured to receive the sample-receiving device, to interface with the mobile device and to communicate information regarding the liquid sample to the mobile device.

6. The device, system or method of any prior embodiment, wherein the first portion comprises a first plate-like portion, and the second portion comprises a second plate-like portion.

7. The device, system or method of any prior embodiment, wherein each of the plurality of first projections and second projections comprises a rectangular cuboid extending perpendicularly from the sample-receiving surface.

8. The device, system or method of any prior embodiment, wherein the first height of the first plurality of projections is less than the second height of the second plurality of projections.

9. The device, system or method of any prior embodiment, wherein the first portion includes a bottom surface, and the first and second regions of the sample-receiving surface are substantially parallel to the bottom surface, and a thickness of the first portion as defined between the first region of the sample-receiving surface and the bottom portion is greater than a thickness of the first portion as defined between the second region of the sample-receiving surface and the bottom portion.

10. The device, system or method of any prior embodiment, wherein a first volume defined as a length of the first region times a width of the first region times the first height of the first plurality of projections, is less than a second volume defined as a length of the second region times a width of the second region times the second height of the first plurality of projections.

11. The device, system or method of any prior embodiment, further comprising a reagent forming a coating over the first region and the second region, the coating having a substantially uniform thickness in each of the first and second regions of the sample-receiving surface.

12. The device, system or method of any prior embodiment, wherein the first and second regions define first and second binding sites, respectively, each of the first and second binding sites comprising a capture agent for binding and immobilizing an analyte of the liquid sample.

13. The device, system or method of any prior embodiment, wherein the first plurality of projections are distributed equidistantly from one another in a lengthwise direction, from a first end toward a second, opposite end.

14. The device, system or method of any prior embodiment, wherein the first plurality of projections are distributed equidistantly from one another in a widthwise direction, from a first side to a second side, in a direction perpendicular to the lengthwise direction.

15. The device, system or method of any prior embodiment, wherein a distance between adjacent projections of the first plurality of projections in the widthwise direction is greater than a distance between adjacent projections of the first plurality of projections in the lengthwise direction.

16. The device, system or method of any prior embodiment, wherein the first volume consists of a first liquid-receiving volume and a first volume occupied by the first plurality of spacers, and the second volume consists of a second liquid-receiving volume and a second volume occupied by the second plurality of spacers, wherein the first liquid-receiving volume is different from the second liquid-receiving volume.

17. The device, system or method of any prior embodiment, further comprising a reagent forming a coating over the first area and the second area, the coating having a substantially uniform thickness in each of the first and second areas, such that a ratio of analytes of the liquid sample to reagent in the first liquid-receiving volume is different from a ratio of analytes of the liquid sample to reagent in the second liquid-receiving volume.

18. The device, system or method of any prior embodiment, wherein the receiving surface is continuous between the first area and the second area such that no fluidic isolation barriers are present between the first area and the second area.

19. The device, system or method of any prior embodiment, wherein a minimum distance from the first area to the second area is determined based upon an expected time required for the liquid sample to laterally diffuse across the receiving surface from the first area to the second area and the time to analyze the liquid sample.

20. The device, system or method of any prior embodiment, wherein the first portion is connected to the second portion by a hinge.

21. The device, system or method of any prior embodiment, wherein the hinge is configured to maintain contact between the first portion and the second portion.

22. The device, system or method of any prior embodiment, wherein the first height of the first plurality of spacers is less than the second height of the second plurality of spacers.

23. The device, system or method of any prior embodiment, wherein each of the first plurality of spacers includes a first top surface substantially parallel to the first area of the receiving surface, and each of the second plurality of spacers includes a second top surface substantially parallel to the second area of the receiving surface, and a total area of the first top surface is less than a total area of the second top surface.

24. The device, system or method of any prior embodiment, wherein each of the first and the second portions comprise rectangular plates, each plate defining a length and width, the lengths of the plates being substantially the same length, and the widths of the plates being substantially the same width.

25. The device, system or method of any prior embodiment, wherein the top surface of the first portion comprises top surfaces of each of the first plurality of spacers and the second plurality of spacers.

26. The device, system or method of any prior embodiment, wherein each of the first plurality of spacers project perpendicularly from the first region of the receiving surface, and each of the second plurality of spacers project perpendicularly from the second region of the receiving surface.

27. The device, system or method of any prior embodiment, wherein the spacers of the first plurality of spacers are all of a same first size, and the spacers of the second plurality of spacers are all of a same second size, the first size and the second size being the same with the exception of the heights of the spacers.

28. The device, system or method of any prior embodiment, wherein the first plurality of spacers are equidistantly spaced from one another in a widthwise direction, and are equidistantly spaced from one another in a lengthwise direction, the lengthwise direction being perpendicular to the widthwise direction.

29. The device, system or method of any prior embodiment, the receiving surface further defining a third area having a third plurality of spacers projecting from the receiving surface, each of the plurality of third spacers defining a third height, the third height being different from each of the first height and the second height.

30. The device, system or method of any prior embodiment, further comprising a reagent forming a coating over the first area, the second area, and the third area, the coating having a substantially uniform thickness in each of the first, second and third areas of the sample-receiving surface.

BD5. The method of embodiment BD3, wherein the optimal target analyte-related signal is determined by selecting the measured target analyte-related signal within a linear detection range of the assay, wherein the linear detection range is a range of the strength of target analyte-related signal, within which the signal strength has a linear correlation with the amount of the assayed target analyte.

E23. The device or method of any one of prior embodiments, wherein the binding site is defined by a patch of dried reagent.

E24. The device or method of any one of prior embodiments, wherein the binding site is between a pair of electrodes.

In some embodiments, one or both plate inner surfaces comprise one or a plurality of amplification sites that are each capable of amplifying the target analyte-related signal when the target analyte is within 500 nm from an amplification site.

E25. The device or method of any one of prior embodiments, wherein the plates have a thickness of less than 200 µm.

E26. The device or method of any one of prior embodiments, wherein the plates have a thickness of less than 100 µm.

E27. The device or method of any one of prior embodiments, wherein each of the plates has an area of less than 5 cm$^2$.

E28. The device or method of any one of prior embodiments, wherein each of the plates has an area of less than 2 cm$^2$.

E29. The device or method of any one of prior embodiments, wherein at least one of the plates is partially or entirely transparent.

E30. The device or method of any one of prior embodiments, wherein at least one of the plates is made from a flexible polymer.

E31. The device or method of any one of prior embodiments, wherein at least one of the plates is a flexible plate, and the thickness of the flexible plate times the Young's modulus of the flexible plate is in the range of 60 to 75 GPa-µm.

E32. The device or method of any one of prior embodiments, wherein the spacers are spacers with a cross sectional shape selected from round, polygonal, circular, square, rectangular, oval, elliptical, or any combination of the same.

E33. The device or method of any one of prior embodiments, wherein the spacers have a pillar shape and a substantially flat top surface, wherein, for each spacer, the ratio of the lateral dimension of the spacer to its height is at least 1.

E34. The device or method of any one of prior embodiments, wherein each spacer has the ratio of the lateral dimension of the spacer to its height is at least 1.

E35. The device or method of any one of prior embodiments, wherein the minimum lateral dimension of spacer is less than or substantially equal to the minimum dimension of a target analyte in the sample.

E36. The device or method of any one of prior embodiments, wherein the spacers have a density of at least 100/mm$^2$.

E37. The device or method of any one of prior embodiments, wherein the spacers have a density of at least 1000/mm$^2$.

E38. The device or method of any one of prior embodiments, wherein the spacers have a filling factor of at least 1%, wherein the filling factor is the ratio of the spacer area in contact with the layer of uniform thickness to the total plate area in contact with the layer of uniform thickness.

E39. The device or method of any one of prior embodiments, wherein the Young's modulus of the spacers times the filling factor of the spacers is equal or larger than 10 MPa, wherein the filling factor is the ratio of the spacer area in contact with the layer of uniform thickness to the total plate area in contact with the layer of uniform thickness.

E40. The device or method of any one of prior embodiments, wherein at least one of the plates is flexible, and b. for the flexible plate, the fourth power of the inter-spacer-distance (ISD) divided by the thickness of the flexible plate (h) and the Young's modulus (E) of the flexible plate, ISD$^4$/(hE), is equal to or less than 10$^6$ um$^3$/GPa.

E41. The device or method of any one of prior embodiments, wherein the spacers are fixed on a plate by directly embossing the plate or injection molding of the plate.

E42. The device or method of any one of prior embodiments, wherein the materials of the plate and the spacers are independently selected from polystyrene, PMMG, PC, COC, COP, or another plastic.

The invention claimed is:

1. A device for analyzing an analyte contained or suspected of being contained in a sample, comprising:
  a first plate, a second plate, and spacers, wherein:
    (a) the first and second plates are movable relative to each other into different configurations, including an open configuration and a closed configuration;
    (b) the first plate comprises, on its inner surface, a first and a second sample contact areas that are at different locations, and the second plate comprises, on its inner surface, a first and a second sample contact areas that are at different locations and correspond to the first and the second sample contact areas of the first plate, respectively, wherein the first and second sample contact areas of the first and second plates are for contacting a sample that contains or is suspected of containing an analyte;
    (c) each of the spacers has a bottom end fixed on the first plate inner surface and a top end that is distal to the first plate;
    (d) the spacers in each sample contact area have a predetermined uniform height, wherein the uniform spacer height in the first sample contact area is different from the uniform spacer height in the second sample contact area on the first plate; and
    (e) the plate thicknesses of the first plate in the first and second sample contact areas are respectively selected to make the top ends of the spacers in the first and second sample contact areas substantially aligned on the same flat plane;

wherein the uniform spacer height in the first area is in the range of 1.5 μm to 8 μm and the uniform spacer height in the second area is in the range of 10 μm to 120 μm;

wherein in the open configuration, the two plates are partially or entirely separated apart, the spacing between the plates is not regulated by the spacers, and the sample is deposited on one or both of the plates; and wherein the closed configuration is configured after the sample deposition in the open configuration, and in the closed configuration: at least part of the deposited sample is confined by the two plates into a layer that has a respective substantially uniform thickness over each of the first and second sample contact areas, wherein the substantially uniform thickness of the layer in each of the first and second sample contact area is different and is regulated by the plates and the spacers in the respective sample contact areas.

2. The device of claim 1, wherein the plates comprise more than two sample contact areas, wherein the spacer height in each area is uniform but different from the spacer heights in other sample contact areas.

3. The device of claim 1, further comprising one or more reagents that are pre-coated on one or more sample contact areas.

4. The device of claim 1, further comprising a bead in the first and second sample contact areas of the first or second plate, wherein the bead comprises a capture agent immobilized on the surface of the bead.

5. The device of claim 4, wherein the bead comprises the capture agent for CRP immobilized on a surface of the bead.

6. The device of claim 4, wherein the bead has a diameter of 2 μm to 10 μm.

7. The device of claim 4, wherein the bead has a diameter of 1 μm to 20 μm.

8. The device of claim 1, wherein the areas for different spacer height on the plates are arranged in an 1 dimensional or 2 dimensional array.

9. The device of claim 1, wherein the sample comprises blood.

10. The device of claim 1, wherein the sample comprises whole blood without dilution.

11. The device of claim 1, wherein the analyte comprises proteins, small molecules, cells, and nucleic acids.

12. The device of claim 1, wherein the uniform spacer height in the first sample contact area has a spacer height to 5 μm, and the uniform spacer height in the second sample contact area has a spacer height of about 30 μm.

13. The device of claim 1, wherein the uniform spacer height in the first sample contact area has a spacer height of 4 μm to 6 μm, and the uniform spacer height in the second sample contact area has a spacer height of 25 μm to 35 μm.

14. The device of claim 1, wherein the uniform spacer height in the first sample contact area is about 5 μm and is for detection of RBC, WBC, PLT, or MCV; and the uniform spacer height in the second sample contact area is 30 μm and is for detecting WBC, or HgB.

15. The device of claim 14, further comprising an imager for imaging and a processor, wherein the imager takes a first image in the first sample contact area and a second image in second sample contact area, wherein the processor analyzes the first image for detection of RBC, WBC, PLT, or MCV; the second image for detecting WBC, or HgB.

16. The device of claim 15, wherein the processor analyzes the first image and the second image for detecting MCH or MCHC.

17. The device of claim 1, wherein each of the first sample contact area and the second sample contact area of the first or second plate independently has a shape of round, ellipse, rectangle, triangle, polygonal, ring-shaped, or any combination of thereof.

18. The device of claim 1, wherein the first sample contact area and the second sample contact area are arranged in an array form, wherein the array is a periodic, non-periodic array, or periodic in some locations of the plate while non-periodic in other locations.

19. The device of claim 1, wherein the periodic array of the spacers is 1-dimensional or 2-dimensional.

20. The device of claim 1, wherein the periodic array of the spacers is arranged as lattices of square, rectangle, triangle, hexagon, polygon, or any combinations of thereof, where a combination means that different locations of a plate has different spacer lattices.

21. The device of claim 1, wherein each of the first and second sample contact areas of the first and second plates comprises a plurality of sample-contacting areas, the plurality of sample-contacting areas are arranged in a periodic array.

22. The device of claim 21, wherein a edge to edge distance of any two closest sample contact areas of the first or second plate is 0 μm, 5 μm, 10 μm, 30 μm, 50 μm, 100 μm, 500 μm, 1 mm, or in a range between any two of the values.

23. The device of claim 21, wherein a distance between the sample-contacting areas of the first sample contact area of the first or second plate and a distance between the sample-contacting areas of the second sample contact area of the first or second plate are larger than $\sqrt{Dt}$, wherein the D is the analyte diffusion coefficient of target analyte and t is the measurement time.

24. The device of claim 1, further comprising more than two sample contact areas on the first plate and corresponding respective sample contact areas on the second plate, wherein the spacer height for each of the sample contact area pairs is different.

25. The device of claim 1, wherein the spacer height in one of the first sample contact area and the second sample contact area is smaller than the minimum dimension of an analyte.

26. The device of claim 1, wherein the spacer height in the first sample contact area is 3 μm to 6 μm and is for detection of RBC, WBC, PLT, MCV; and the spacer height in the second sample contact area is 25 μm to 35 μm and is for WBC, HgB.

27. The device of claim 26, further comprising an imager for imaging and a processor, wherein the imager takes a first image in the first sample contact area and a second image in second sample contact area, wherein the processor analyzes the first image for detection of RBC, WBC, PLT, or MCV; the second image for detecting WBC, or HgB.

28. The device of claim 27, wherein the processor analyzes the first image and the second image for detecting MCH or MCHC.

29. The device of claim 1, wherein chemicals are coated with a different concentration in different spacer height areas.

30. The device of claim 1, wherein different chemicals are coated with a different concentration in different spacer height areas.

31. The device of claim 1, wherein acridine orange is coated on one of the first and second sample contact areas of the first or second plate with an area concentration of 10 to 80 ng/mm² and Zwittergent is coated on one of the first and second sample contact areas of the first or second plate with an area concentration of 20 to 130 ng/mm$^2$.

32. The device of claim 1, wherein the different spacer heights are selected to reduce the Hook Effect in an assay.

33. The device of claim 1, wherein the spacers in each of the first and second sample contact areas of the first plate are used as the reference for an optical signal during the measurement.

34. The device of claim 1, wherein the spacers in each of the first and second sample contact areas of the first plate are used as the reference for the image correction standard during the measurement.

35. The device of claim 1, wherein the first and second sample contact areas of the first or second plate each comprise a coating of a reagent at a same concentration.

36. The device of claim 1, wherein the first and second sample contact areas of the first or second plate each comprise a coating of a reagent at a different concentration.

37. The device of claim 1, wherein the spacer height in one of the first and second sample contact areas is smaller than the minimum dimension of a cell.

38. The device of claim 1, wherein the analyte comprises blood cell.

39. The device of claim 1, wherein the analyte comprises red blood cells, platelets, white blood cells, neutrophils, lymphocytes, monocytes, eosinophils and basophils, or any combination thereof.

40. The device of claim 1, wherein the shape of a sample is deformable but not self-flowable.

41. The device of claim 1, wherein the first sample contact area of the first or second plate comprises a first reagent, the second sample contact area of the first or second plate comprises a second reagent, the first reagent is different from the second reagent, and the first reagent has a different concentration than the second reagent.

42. The device of claim 1, wherein the first and second sample contact areas of the first or second plate each comprise a coating of different reagents at a same concentration.

43. The device of claim 1, wherein the first and second sample contact areas of the first or second plate comprise a coating of different reagents at different concentration.

44. The device of claim 1, wherein the spacers are arranged periodically.

45. The device of claim 1, wherein the first and second sample contact areas of the first or second plate each comprises a plurality of sample-contacting areas, and the sample-contacting areas have different spacer heights but the same concentration of a reagent.

46. The device of claim 1, further comprising an imager.

47. The device of claim 46, further comprising a processor that analyzes the analyte.

48. The device of claim 47, further comprising a process that has a machine learning algorithm for counting the cells.

49. The device of claim 1, wherein the areas for different spacer height on the plates are arranged in an array form, and the array is periodic.

50. The device of claim 1, wherein the areas for different spacer height on the plates are arranged in an array form, and the array is nonperiodic.

51. A method for analyzing an analyte in a sample, comprising:
(a) obtaining a sample that contains or is suspected of containing an analyte;
(b) obtaining the device of claim 1;
(c) depositing the sample into the device and bring the first and second plates into the closed configuration;
(d) imaging, after (c), using at least one imager, one or more images of the first and/or the second sample contact areas; and
(e) detect the analyte by analyzing the one or more images.

52. The method of claim 51, wherein the ratio of an optical signal in an image of the different sample contact areas is taken with a different spacer height and/or a different reagent surface concentration.

53. The method of claim 51, wherein the one or more images comprise bright field image, fluorescence image, or both.

54. The method of claim 53, wherein the analysis comprises analyzing both the bright field and fluorescence images.

55. The method of claim 51, further comprising checking a linearity of a parameter of an assay or assay operation or both by taking a ratio of an optical parameter of two sample contact areas of different spacing heights, wherein the optical parameter is extracted from the image of each of the sample contact areas and the spacing heights are predetermined.

56. The method of claim 51, further comprising checking and correcting a nonlinearity of a parameter of an assay by taking a ratio of an optical parameter of more than two sample contact areas of different spacing heights, wherein the optical parameter is extracted from the image of each of the more than two sample contact areas and the spacing heights are predetermined.

57. The method of claim 51, further comprising getting information of different analytes in the same sample with different spacing heights.

58. The method of claim 51, further comprising getting information of different analytes in the same sample with different spacing heights and different reagents in different heights.

59. The method of claim 51, further comprising monitoring the spacing height during measurement by comparing the optical parameter of two sample contact areas of different spacing heights.

60. The method of claim 51, wherein the detection of the analyte is for blood cell test, that tests white blood cell count (WBC or leukocyte count), WBC differential count, Red blood cell count or erythrocyte count, Hematocrit (Hct), Hemoglobin (Hbg), Mean corpuscular volume (MCV), Mean corpuscular hemoglobin (MCH), Mean corpuscular hemoglobin concentration (MCHC), Red cell distribution width (RDW), Platelet count, Mean Platelet Volume (MPV).

61. The method of claim 51, further comprising measuring same sample in different height in the same device to reduce the statistic error.

62. The method of claim 51, further comprising getting information of analytes distribution when flowing in the device with different spacing heights.

63. The method of claim 51, wherein the analyte detection comprises blood cell tests, blood tests, liver function tests, renal function tests, uric acid tests, hepatitis tests, tumors markers tests, thyroid function tests, tissue inflammation screening, sexually transmitted disease screening, blood grouping tests, urinalysis, fecal occult blood tests, smear screening; allergies and sensitivities tests, biochemical tests, gmelin's test, organic tests, inorganic tests, general chemical tests, parameter tests including density, nitrogen content, foaming propensity, emulsion stability and others; water, effluent & sludge analysis, and eco parameters tests.

64. The method of claim 51, further comprising more than two sample contact areas, wherein each sample contact area has a uniform spacer height.

65. The method of claim 51, further comprising one or more reagents that are pre-coated on one or more sample contact areas.

66. The method of claim 51, further comprising one or more beads in the sample contact areas, wherein the beads comprise capture agents immobilized on the surface of the beads.

67. The method of claim 66, wherein the beads comprise the capture agent for CRP immobilized on the bead surface.

68. The method of claim 66, wherein the beads have a diameter of 2 μm to 10 μm.

69. The method of claim 66, wherein the beads have a diameter of 1 μm to 20 μm.

70. The method of claim 51, wherein the periodic array of the spacers is arranged in 1 dimensional or 2 dimensional.

71. The method of claim 51, wherein the sample comprises blood.

72. The method of claim 51, wherein the sample comprises whole blood without dilution.

73. The method of claim 51, wherein the analyte comprises proteins, small molecules, cells, and nucleic acids blood.

74. The method of claim 51, wherein the uniform spacer height in the first sample contact area has a spacer height to 5 μm, and the uniform spacer height in the second sample contact area has a spacer height of about 30 μm.

75. The method of claim 51, wherein the uniform spacer height in the first sample contact area has a spacer height of 4 μm to 6 μm, and the uniform spacer height in the second sample contact area has a spacer height of 25 μm to 35 μm.

76. The method of claim 51, wherein the uniform spacer height in the first sample contact area is about 5 μm and is for detection of RBC, WBC, PLT, MCV; and the uniform spacer height in the second sample contact area is 30 μm and is for WBC, HgB, and the images taken at the first sample contact area and second sample contact area are combined for detection of MCH, MCHC.

77. The method of claim 51, wherein the first sample contact area and the second sample contact area include a shape of round, ellipse, rectangle, triangle, polygonal, ring-shaped, or any combination of thereof.

78. The method of claim 51, wherein the first sample contact area and the second sample contact area are arranged in an array form, wherein the array is a periodic, non-periodic array, or periodic in some locations of the plate while non-periodic in other locations.

79. The method of claim 51, wherein the periodic array of the spacers is 1-dimensional or 2-dimensional.

80. The method of claim 51, wherein the periodic array of the spacers is arranged as lattices of square, rectangle, triangle, hexagon, polygon, or any combinations of thereof, where a combination means that different locations of a plate has different spacer lattices.

81. The method of claim 51, wherein the first sample contact area and the second sample contact area are arranged in a periodic array.

82. The method of claim 51, further comprising more than two sample contact areas on the first plate and corresponding respective sample contact areas on the second plate, wherein the spacing height for each of the sample contact area pairs is different.

83. The method of claim 51, wherein the spacer height in one of the first sample contact area and the second sample contact area is smaller than the minimum dimension of an analyte.

84. The method of claim 51, wherein the spacer height in the first sample contact area is 3 μm to 6 μm and is for detection of RBC, WBC, PLT, MCV; and the spacer height in the second sample contact area is 25 μm to 35 μm and is for WBC, HgB, and the images taken at the first and second sample contact areas are combined for detection of MCH, MCHC.

85. The method of claim 51, wherein chemicals are coated with a different concentration in different spacer height areas.

86. The method of claim 51, wherein different chemicals are coated with a different concentration in different spacer height areas.

87. The method of claim 51, wherein acridine orange is coated on the plate at one of the first and second sample contact areas with an area concentration of 10 to 80 ng/mm$^2$ and Zwittergent is coated on the plate at one of the first and second sample contact areas with an area concentration of 20 to 130 ng/mm$^2$.

88. The method of claim 51, wherein the preferred edge to edge distance of any two closest sample contact areas is 0 μm, 5 μm, 10 μm, 30 μm, 50 μm, 100 μm, 500 μm, 1 mm, or in a range between any two of the values.

89. The method of claim 51, wherein the different spacer heights are selected to reduce the Hook Effect in an assay.

90. The method of claim 51, wherein the spacers in each sample contact area are used as the reference for an optical signal during the measurement.

91. The method of claim 51, wherein the spacers in each sample contact area are used as the reference for the image correction standard during the measurement.

92. The method of claim 51, wherein the distance between the first sample contact area and the distance between the second sample contact area is larger than $\sqrt{Dt}$, wherein a D is the analyte diffusion coefficient of target analyte and t is the measurement time.

93. The method of claim 51, wherein the different sample contact areas comprise a coating of the reagent of the same surface concentration.

94. The method of claim 51, wherein each of the different sample contact areas comprise a coating of the reagent of a different surface concentration.

95. The method of claim 51, wherein the spacer height in one of the first and second sample contact areas is smaller than the minimum dimension of a cell.

96. The method of claim 51, wherein the analyte comprises blood cell.

97. The method of claim 51, wherein the analyte comprises red blood cells, platelets, white blood cells, neutrophils, lymphocytes, monocytes, eosinophils and basophils, or any combination thereof.

98. The method of claim 51, wherein the shape of a sample is deformable but not self-flowable.

99. Method of claim 51, wherein one of the sample contact areas include a reagent of the same surface concentration, which is different from the reagent surface concentration of another of the sample contact areas.

100. The method of claim 51, wherein different sample contact areas comprise coating of different reagents types of the same surface concentration.

101. The method of claim 51, wherein different sample contact areas comprise coating of different reagents types of different surface concentration.

102. The method of claim 51, wherein the spacers are arranged periodically.

103. The method of claim 51, wherein the dynamic range of measurement of an assay is enlarged by having a plurality of sample contact areas of different spacer height but the same surface concentration of the reagent.

* * * * *